US008103337B2

(12) United States Patent
Graovac et al.

(10) Patent No.: US 8,103,337 B2
(45) Date of Patent: Jan. 24, 2012

(54) WEIGHTED GRADIENT METHOD AND SYSTEM FOR DIAGNOSING DISEASE

(75) Inventors: Milan Graovac, Toronto (CA); James Martens, Toronto (CA); Zoran Pavlovic, Toronto (CA); Joel Ironstone, Toronto (CA)

(73) Assignee: Impedimed Limited, Queensland (AU)

( * ) Notice: Subject to any disclaimer, the term of this patent is extended or adjusted under 35 U.S.C. 154(b) by 1515 days.

(21) Appl. No.: 11/287,470

(22) Filed: Nov. 28, 2005

(65) Prior Publication Data

US 2006/0151815 A1 Jul. 13, 2006

Related U.S. Application Data

(60) Provisional application No. 60/630,566, filed on Nov. 26, 2004.

(51) Int. Cl.
*A61B 5/05* (2006.01)
*G06T 17/00* (2006.01)
*G09G 5/02* (2006.01)
(52) U.S. Cl. ............ 600/547; 345/424; 345/600
(58) Field of Classification Search .......... 345/424, 345/600; 600/547
See application file for complete search history.

(56) References Cited

U.S. PATENT DOCUMENTS

| | | | |
|---|---|---|---|
| 3,316,896 A | 5/1967 | Thomasset | |
| 3,851,641 A | 12/1974 | Toole et al. | |
| 3,871,359 A | 3/1975 | Pacela | |
| 4,008,712 A | 2/1977 | Nyboer | |
| 4,034,854 A | 7/1977 | Bevilacqua | |
| 4,144,878 A | 3/1979 | Wheeler | |
| 4,184,486 A | 1/1980 | Papa | |
| 4,291,708 A | 9/1981 | Frei et al. | |
| 4,314,563 A | 2/1982 | Wheeler | |
| 4,365,634 A | 12/1982 | Bare et al. | |
| 4,407,288 A | 10/1983 | Langer et al. | |
| 4,407,300 A | 10/1983 | Davis | |
| 4,450,527 A | 5/1984 | Sramek | |
| 4,458,694 A | 7/1984 | Sollish et al. | |

(Continued)

FOREIGN PATENT DOCUMENTS

CA 2231038 A1 11/1999

(Continued)

OTHER PUBLICATIONS

International Preliminary Reproort on Patentability for PCT/CA2004/000458 dated Jan. 10, 2005.*

(Continued)

*Primary Examiner* — Max Hindenburg
*Assistant Examiner* — Sean P Dougherty
(74) *Attorney, Agent, or Firm* — Bereskin & Parr LLP/S.E.N.C.R.L., s.r.l.

(57) ABSTRACT

A method for detecting and diagnosing disease states in a body part is described. The method starts with a preparatory step of modeling the body part as a grid of many finite elements, then calculating an electrical property between two finite elements at which current from two corresponding electrodes flows through the body part. This is termed the weight (influence) of the element. With this baseline information, electrical impedance measurements made at the plurality of electrodes on the periphery of the body part can be used in a diagnostic module to calculate a Weighted Element Value (WEVal) for each element. In a preferred embodiment of invention, the difference in WEVal magnitude between corresponding elements of homologous body parts serves as an indicator of the presence of disease.

23 Claims, 10 Drawing Sheets

U.S. PATENT DOCUMENTS

| | | |
|---|---|---|
| 4,468,835 A | 9/1984 | Bai et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,895,163 A | 1/1990 | Libke et al. |
| 4,911,175 A | 3/1990 | Shizgal |
| 4,942,880 A | 7/1990 | Slovak |
| 4,951,682 A | 8/1990 | Petre |
| 5,025,784 A | 6/1991 | Shao et al. |
| 5,063,937 A | 11/1991 | Ezenwa et al. |
| 5,143,079 A | 9/1992 | Frei et al. |
| 5,166,876 A | 11/1992 | Cline et al. |
| 5,197,479 A | 3/1993 | Hubelbank et al. |
| 5,246,008 A | 9/1993 | Mueller |
| 5,280,429 A | 1/1994 | Withers |
| 5,305,192 A | 4/1994 | Bonte et al. |
| 5,311,878 A | 5/1994 | Brown et al. |
| 5,315,512 A | 5/1994 | Roth |
| 5,372,141 A | 12/1994 | Gallup |
| 5,415,164 A | 5/1995 | Faupel et al. |
| 5,449,000 A | 9/1995 | Libke et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,506,785 A | 4/1996 | Blank et al. |
| 5,529,072 A | 6/1996 | Sramek |
| 5,544,662 A | 8/1996 | Saulnier et al. |
| 5,557,242 A | 9/1996 | Wetherell |
| 5,588,429 A | 12/1996 | Isaacson et al. |
| 5,704,355 A | 1/1998 | Bridges |
| 5,732,710 A | 3/1998 | Rabinovich et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,919,142 A | 7/1999 | Boone et al. |
| 6,011,992 A | 1/2000 | Hubbard et al. |
| 6,015,389 A | 1/2000 | Brown |
| 6,018,677 A | 1/2000 | Vidrine et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Rosell Ferrer et al. |
| 6,173,003 B1 | 1/2001 | Whikehart et al. |
| 6,228,022 B1 | 5/2001 | Friesem et al. |
| 6,233,473 B1 | 5/2001 | Shepherd et al. |
| 6,236,886 B1 | 5/2001 | Cherepenin et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,496,725 B2 | 12/2002 | Kamada et al. |
| 6,532,384 B1 | 3/2003 | Fukuda |
| 6,569,160 B1 | 5/2003 | Goldin et al. |
| 6,584,348 B2 | 6/2003 | Glukhovsky |
| 6,618,616 B2 | 9/2003 | Iijima et al. |
| 6,625,487 B2 | 9/2003 | Herleikson |
| 6,631,292 B1 | 10/2003 | Liedtke |
| 6,633,777 B2 | 10/2003 | Szopinski |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,760,617 B2 | 7/2004 | Ward et al. |
| 6,768,921 B2 | 7/2004 | Organ et al. |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 7,130,680 B2 | 10/2006 | Kodama et al. |
| 7,148,701 B2 | 12/2006 | Park et al. |
| 7,212,852 B2 | 5/2007 | Smith et al. |
| 7,457,660 B2 | 11/2008 | Smith et al. |
| 7,477,937 B2 | 1/2009 | Iijima et al. |
| 7,706,872 B2 | 4/2010 | Min et al. |
| 7,733,224 B2 | 6/2010 | Tran |
| 2001/0007056 A1 | 7/2001 | Linder et al. |
| 2001/0020138 A1 | 9/2001 | Ishigooka et al. |
| 2001/0025139 A1 | 9/2001 | Pearlman |
| 2002/0072686 A1 | 6/2002 | Hoey et al. |
| 2002/0079910 A1 | 6/2002 | Fukuda |
| 2002/0093991 A1 | 7/2002 | Plangger |
| 2002/0093992 A1 | 7/2002 | Plangger |
| 2002/0123694 A1 | 9/2002 | Organ et al. |
| 2002/0161311 A1 | 10/2002 | Ward et al. |
| 2002/0194419 A1 | 12/2002 | Rajput et al. |
| 2003/0004403 A1 | 1/2003 | Drinan et al. |
| 2003/0050570 A1 | 3/2003 | Kodama et al. |
| 2003/0073916 A1 | 4/2003 | Yonce |
| 2003/0105411 A1 | 6/2003 | Smallwood et al. |
| 2004/0015095 A1 | 1/2004 | Li et al. |
| 2004/0077944 A1 | 4/2004 | Steinberg et al. |
| 2004/0158167 A1 | 8/2004 | Smith et al. |
| 2004/0167423 A1 | 8/2004 | Pillon et al. |
| 2004/0181164 A1 | 9/2004 | Smith et al. |
| 2004/0186392 A1 | 9/2004 | Ward et al. |
| 2004/0210150 A1 | 10/2004 | Virtanen |
| 2004/0210158 A1 | 10/2004 | Organ et al. |
| 2004/0252870 A1* | 12/2004 | Reeves et al. ............... 382/128 |
| 2005/0033281 A1 | 2/2005 | Bowman et al. |
| 2005/0098343 A1 | 5/2005 | Fukuda |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2006/0004300 A1 | 1/2006 | Kennedy |
| 2006/0085048 A1 | 4/2006 | Cory et al. |
| 2006/0085049 A1 | 4/2006 | Cory et al. |
| 2006/0116599 A1 | 6/2006 | Davis |
| 2006/0122523 A1 | 6/2006 | Bonmassar et al. |
| 2006/0197509 A1 | 9/2006 | Kanamori et al. |
| 2006/0224079 A1 | 10/2006 | Washchuk |
| 2006/0224080 A1 | 10/2006 | Oku et al. |
| 2006/0270942 A1 | 11/2006 | McAdams |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0087703 A1 | 4/2007 | Li et al. |
| 2007/0106342 A1 | 5/2007 | Schumann |
| 2008/0002873 A1* | 1/2008 | Reeves et al. ............... 382/133 |
| 2008/0004904 A1 | 1/2008 | Tran |
| 2008/0009757 A1 | 1/2008 | Tsoglin et al. |
| 2008/0039700 A1 | 2/2008 | Drinan et al. |
| 2008/0205717 A1* | 8/2008 | Reeves et al. ............... 382/128 |
| 2008/0319336 A1 | 12/2008 | Ward et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0105555 A1 | 4/2009 | Dacso et al. |
| 2009/0177099 A1 | 7/2009 | Smith et al. |
| 2009/0264776 A1 | 10/2009 | Vardy |
| 2009/0287102 A1 | 11/2009 | Ward |
| 2009/0318778 A1 | 12/2009 | Dacso et al. |
| 2010/0145164 A1 | 6/2010 | Howell |
| 2010/0168530 A1 | 7/2010 | Chetham et al. |
| 2010/0234701 A1 | 9/2010 | Cho et al. |

FOREIGN PATENT DOCUMENTS

| | | |
|---|---|---|
| CA | 2528303 A1 | 5/2006 |
| DE | 2912349 A1 | 10/1980 |
| EP | 0249823 A | 12/1987 |
| EP | 349043 A2 | 1/1990 |

| | | | |
|---|---|---|---|
| EP | 0357309 A | 7/1990 | |
| EP | 377887 A1 | 7/1990 | |
| EP | 0373854 | 10/1997 | |
| EP | 0869360 A | 7/1998 | |
| EP | 865763 A | 9/1998 | |
| EP | 1114610 A1 | 7/2001 | |
| EP | 1146344 A | 10/2001 | |
| EP | 1177760 A1 | 2/2002 | |
| EP | 1219937 A | 7/2002 | |
| EP | 1338246 A1 | 8/2003 | |
| EP | 1452131 A | 1/2004 | |
| EP | 1629772 A1 | 3/2006 | |
| EP | 1827222 A1 | 9/2007 | |
| FR | 2486386 A1 | 1/1982 | |
| GB | 2131558 A | 6/1984 | |
| GB | 2260416 A | 4/1993 | |
| GB | 2426824 A1 | 12/2006 | |
| JP | 09051884 A | 2/1997 | |
| JP | 9220209 A | 8/1997 | |
| JP | 10000185 A | 1/1998 | |
| JP | 10014898 A | 1/1998 | |
| JP | 10014899 A | 2/1998 | |
| JP | 10-225521 A | 8/1998 | |
| JP | 11070090 A | 3/1999 | |
| JP | 2000139867 A | 5/2000 | |
| JP | 2001321352 A | 11/2001 | |
| JP | 2002330938 A | 11/2002 | |
| JP | 2008022995 A | 7/2008 | |
| SU | 1132911 A | 7/1985 | |
| WO | 88/07392 A | 10/1988 | |
| WO | 96/12439 A1 | 5/1996 | |
| WO | 96/32652 A1 | 10/1996 | |
| WO | 97/11638 A | 4/1997 | |
| WO | 98/23204 A1 | 6/1998 | |
| WO | 98/33553 A | 8/1998 | |
| WO | 00/40955 A1 | 7/2000 | |
| WO | 00/79255 A1 | 12/2000 | |
| WO | 01/50954 A1 | 7/2001 | |
| WO | 01/67098 A1 | 9/2001 | |
| WO | 02/062214 A | 8/2002 | |
| WO | 02/094096 A1 | 11/2002 | |
| WO | 2004/000115 A1 | 12/2003 | |
| WO | 2004/026136 A1 | 1/2004 | |
| WO | 2004/047635 A1 | 6/2004 | |
| WO | 2004/049936 A2 | 6/2004 | |
| WO | 2004/083804 A2 | 9/2004 | |
| WO | WO 2004/084724 | 10/2004 | |
| WO | 2005/010640 A2 | 2/2005 | |
| WO | 2005/027717 A2 | 3/2005 | |
| WO | 2005/051194 A1 | 6/2005 | |
| WO | 2005/122888 A1 | 12/2005 | |
| WO | 2006/056074 A1 | 6/2006 | |
| WO | 2006/129108 A1 | 12/2006 | |
| WO | 2006/129116 A1 | 12/2006 | |
| WO | 2007/002991 A1 | 1/2007 | |
| WO | 2007/002992 A1 | 1/2007 | |
| WO | 2007/002993 A1 | 1/2007 | |
| WO | 2007/014417 A1 | 2/2007 | |
| WO | 2007/041783 A1 | 4/2007 | |
| WO | 2008/064426 A1 | 6/2008 | |
| WO | 2008/119166 A1 | 9/2008 | |
| WO | 2008/138062 A1 | 11/2008 | |
| WO | 2009/100491 A1 | 8/2009 | |

OTHER PUBLICATIONS

Written Opinion of the International Searching Authority for PCT/CA/2004/000458 dated Mar. 26, 2004.*

Dines K A et al: "Analysis of Electrical Conductivity Imaging" Geophysics Jul. 1981, vol. 46, No. 7, Jul. 1981, pp. 1025-1036, XP002288671.*

Osterman K S et al: "Multifrequency electrical impedance imaging: preliminary in vivo experience in breast" Physiol. Meas. (UK), Physiological Measurement, IOP Publishing, UK, vol. 21, No. 1, Feb. 2000, pp. 99-109, XP002288672 ISSN: 0967-3334.*

Abdullah M Z: "Simulation of an inverse problem in electrical impedance tomography using resistance electrical network analogues" Int. J. Electr. Eng. Educ. (UK), International Journal of Electrical Engineering Education, Manchester University Press, UK, vol. 36, No. 4, Oct. 1999, pp. 31 1-324, XP008032914 ISSN: 0020-7209.*

Abdullah M. Z., Simulation of an inverse problem in electrical impedance tomography using resistance electrical network analogues, International Journal of Electrical Engineering Education, Jan. 10, 1999, vol. 36, No. 4, pp. 311-324.

Al-Hatib, F., Patient Instrument connection errors in bioelectrical impedance measurement, Physiological Measurement, Feb. 5, 1998, vol. 19, No. 2, pp. 285-296.

Steijaert, M. et al, The use of multi-frequency impedance to determine total body water and extracellular water in obese and lean female individuals, International Journal of Obesity, 1997, vol. 21, pp. 930-934.

Surowiec, A.J. et al., Dielectric Properties of Brest Carcinima and the Surrounding Tissues, IEEE Transactions on Biomedical Engineering, 1988, vol. 35, pp. 257-263.

Tedner, B., Equipment Using Impedance Technique for Automatic Recording of Fluid-Volume Changes During Haemodialysis, Medical & Biological Engineering & Computing, 1983, pp. 285-290.

Thomas. B.J., Future Technologies, Asia Pacific Journal Clinical Nutrition 1995, vol. 4, pp. 157-159.

Thomas. B.J. et al., Bioimpedance Spectrometry in Determination of Body Water Compartments: Accuracy and Clinical Significance, Applied Radiation and Isotopes 1998, vol. 49, No. 5/6, pp. 447-455.

Boulier, A. et al., Fat-Free Mass Estimation by Two Electrode Impedance Method, American Journal of Clinical Nutrition, 1990, vol. 52, pp. 581-585.

Bracco, D. et al., Bedside determination of fluid accumulation after cardiac surgery using segmental bioelectrical impedance, Critical Care Medicine 1998, vol. 26, No. 6, pp. 1065-1070.

Chaudary, S.S. et al., Dielectric Properties of Normal & Malignant Human Breast Tissues at Radiowave and Microwave Frequencies, Indian Journal of Biochemistry & Biophysics 1984, vol. 21, No. 1, pp. 76-79.

Chiolero, R.L. et al., Assessment of changes in body water by bioimpedance in acutely ill surgical patients, Intensive Care Medicine 1992, vol. 18, pp. 322-326.

Chumlea et al., Bioelectrical Impedance and Body Composition: Present Status and Future Directions, Nutrition Reviews 1994, vol. 52, No. 4, pp. 123-131.

Cornish, B.H. et al., Quantification of Lymphoedema using Multi-frequency Bioimpedance, Applied Radiation and Isotopes 1998, vol. 49, No. 5/6, pp. 651-652.

Cornish, B.H. et al., Bioelectrical impedance for monitoring the efficacy of lymphoedema treatment programmes, Breast Cancer Research and Treatment 1996, vol. 38, pp. 169-176.

Cornish, B.H. et al., Data analysis in multiple-frequency bioelectrical impedance analysis, Physiological Measurement Jan. 5, 1998, vol. 19, No. 2, pp. 275-283.

Cornish, B.H. et al., Alteration of the extracellular and total body water volumes measured by multiple frequency bioelectrical impedance analysis, Nutrition Research 1994, vol. 14, No. 5, pp. 717-727.

Cornish, B.H. et al., Early diagnosis of lymphedema using multiple frequency bioimpedance, Lymphology Jan. 3, 2001, vol. 34, pp. 2-11.

Cornish, B.H. et al., Early diagnosis of lymphoedema in postsurgery breast cancer patients, Annals New York Academy of Sciences Jan. 5, 2000, pp. 571-575.

De Luca, F. et al., Use of low-frequency electrical impedance measurements to determine phospoholipid content in amniotic fluid, Physics in Medicine and Biology 1996, vol. 41, pp. 1863-1869.

Deurenberg, P. et al., Multi-frequency bioelectrical impedance: a comparison between the Cole-Cole modelling and Hanai equations with the classicaly impedance index approach, Annals of Human Biology 1996, vol. 23, No. 1, pp. 31-40.

Dines K.A. et al., Analysis of electrical conductivity imaging, Geophysics Jan. 7, 1981, vol. 46, No. 7, pp. 1025-1036.

Ellis, K. J. et al., Human hydrometry: comparison of multifrequency bioelectrical impedance with 2H20 and bromine dilution, Journal of Applied Physiology 1998, vol. 85, No. 3, pp. 1056-1062.

Forslund, A.H. et al., Evaluation of modified multicompartment models to calculate body composition in healthy males, American Journal of Clinical Nutrition 1996, vol. 63, pp. 856-62.

Gersing, E., Impedance spectroscopy on living tissue for determination of the state of organs, Bioelectrochemistry and Bioenergetics, 1998, vol. 45, pp. 145-149.

Gerth, W.A. et al., A computer-based bioelectrical impedance spectroscopic system for noninvasive assessment of compartmental fluid redistribution, Third Annual IEEE Symposium on Computer Based Medical Systems, Jun. 3-6, 1990, University of NC. At Chapel Hill, Jan. 6, 1990, pp. 446-453.

Gudivaka R. et al., Single- and multifrequency models for bioelectrical impedance analysis of body water compartments, Applied Physiology, 1999, vol. 87, Issue 3, pp. 1087-1096.

Jones CH et al., Extracellular fluid volume determined by bioelectric impedance and serum albumin in CAPD patients, Nephrology Dialysis Transplantation, 1998, vol. 13, pp. 393-397.

Jossinet, J. et al., A Study for Breast Imaging with a Circular Array of Impedance Electrodes, Proc. Vth Int. Conf. Bioelectrical Impedance, 1981, Tokyo, Japan, 1981, pp. 83-86.

Jossinet, J. et al.,Technical Implementation and Evaluation of a Bioelectrical Breast Scanner, Proc. 10.sup.th Int. Conf. IEEE Engng. Med. Biol., 1988, New Orleans, USA (Imped. Imaging II), 1988, vol. 1. p. 289.

Kanai, H. et al., Electrcial Measurment of Fluid Distribution in Legs and Arms, Medical Progress through technology, 1987, pp. 159-170.

Kim, C.T. et al., Bioelectrical impedance changes in regional extracellular fluid alterations, Electromyography and Clinical Neurophysiology, 1997, vol. 37, pp. 297-304.

Lozano, A. et al., Two-frequency impedance plethysmograph: real and imaginary parts, Medical & Biological Engineering & Computing, Jan. 1, 1990, vol. 28, No. 1, pp. 38-42.

Liu R. et al., Primary Multi-frequency Data Analyze in Electrical Impedance Scanning, Proceedings of the IEEE-EMBS 2005, 27th Annual International Conference of the Engineering in Medicine and Biology Society, Shanghai, China, Sep. 1-4, 2005, pp. 1504-1507.

Lukaski, H.C. et al., Estimation of Body Fluid Volumes Using Tetrapolar Bioelectrical Impedance Measurements, Aviation, Space, and Environmental Medicine, Jan. 12, 1988, pp. 1163-1169.

Man, B. et al., Results of Preclinical Tests for Breast Cancer Detection by Dielectric Measurements, XII Int. Conf. Med. Biol. Engng. 1979, Jerusalem, Israel. Springer Int., Berlin, 1980, Section 30.4.

Mattar, J.A., Application of Total Body Impedance to the Critically Ill Patient, New Horizons, 1996, vol. 4, No. 4, pp. 493-503.

McDougal D., et al., Body Composition Measurements From Whole Body Resistance and Reactance, Surgical Forum, 1986, vol. 36, pp. 43-44.

Osterman K.S. et al., Multifrequency electrical impedance imaging: preliminary in vivo experience in breast, Physiological Measurement, Jan. 2, 2000, vol. 21, No. 1, pp. 99-109.

Ott, M. et al., Bioelectrical Impedance Analysis as a Predictor of Survival in Patients with Human Immunodeficiency Virus Infection, Journal of Acquired Immune Deficiency Syndromes and Human Retrovirology, 1995, vol. 9, pp. 20-25.

Pethig, R. R et al., The Passive Electrical Properties of Biological Systems: Their Significance in Physiology, Biophysics and Biotechnology, Physics in Medicine and Biology, 1987, vol. 32, pp. 933-970.

Piperno, G. et al., Breast Cancer Screening by Impedance Measurements, Frontiers of Medical & Biological Engineering, 1990, vol. 2, pp. 111-117.

Rigaud, B. et al., Bioelectrical Impedance Techniques in Medicine, Critical Reviews in Biomedical Engineering, 1996, vol. 24 (4-6), pp. 257-351.

Schneider, I., Broadband signals for electrical impedance measurements for long bone fractures, Engineering in Medicine and Biology Society, 1996. Bridging Disciplines for Biomedicine. Proceedings of the 18th Annual International Conference of the IEEE, Oct. 31,1996, vol. 5, pp. 1934-1935.

Skidmore, R. et al., A Data Collection System for Gathering Electrical Impedance Measurements from the Human Breast, Clinical Physics Physiological Measurement, 1987, vol. 8, pp. 99-102.

Sollish, B.D. et al., Micropressor-assisted Screening Techniques, Israel Journal of Medical Sciences, 1981, vol. 17, pp. 859-864.

Thomas. B.J. et al., Bioelectrical impedance analysis for measurement of body fluid volumes—A review, Journal of Clinical Engineering, 1992, vol. 17, No. 16, pp. 505-510.

Ulgen, Y. et al., Electrical parameters of human blood, Engineering in Medicine and Biology Society, 1998. Proceedings of the 20th Annual International Conference of the IEEE, Jan. 11, 1998, vol. 6, pp. 2983-2986.

Ward, L.C. et al., Multi-frequency bioelectrical impedance augments the diagnosis and management of lymphoedema in post-mastectomy patients, European Journal of Clinical Investigation, 1992, vol. 22, pp. 751-754.

Ward, L.C. et al., Determination of Cole parameters in multiple frequency bioelectrical impedance analysis using only the measurement of impedances; Four-frequency fitting, Physiological Measurement, Jan. 9, 2006, vol. 27, No. 9, pp. 839-850.

Woodrow, G. et al., Effects of icodextrin in automated peritoneal dialysis on blood pressure and bioelectrical impedance analysis, Nephrology Dialysis Transplantation, 2000, vol. 15, pp. 862-866.

Breckon, W.R. et al, Mathematical aspects of impedance imaging, Clinical Physics Physiological Measurement, 1987, vol. 8, pp. 77-87.

Barber. D.C. et al, Errors in reconstruction of resistivity images using a linear reconstruction technique, Clinical Physics Physiological Measurement, 1988, vol. 9, pp. 101-104.

Ward, L.C. et al., There is a better way to measure Lymphodema, National Lymphedema Network Newsletter, Oct. 1995, vol. 7, No. 4, pp. 89-92.

* cited by examiner

Right Breast
Left Breast
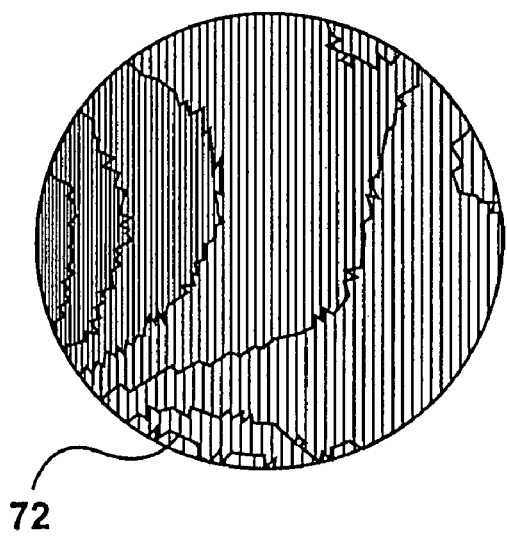
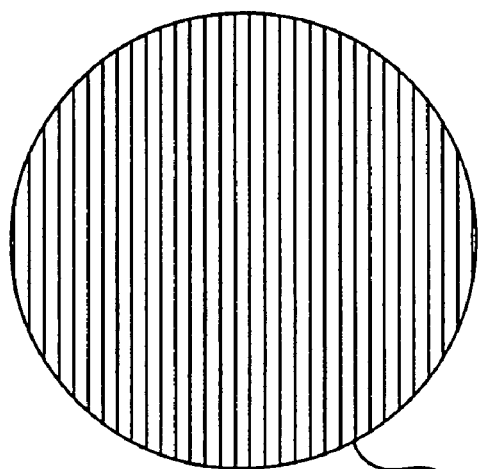
72
74
FIG. 6A
FIG. 6B

WEIGHTED GRADIENT METHOD AND SYSTEM FOR DIAGNOSING DISEASE

This application claims the benefit of U.S. Provisional Application No. 60/630,566, filed Nov. 26, 2004, and the entire contents of which are hereby incorporated by reference.

FIELD OF THE INVENTION

This invention relates to a method for detecting and diagnosing disease states in living organisms and specifically relates to diagnosis of disease by measuring electrical properties of body parts.

BACKGROUND OF THE INVENTION

Several methods exist for diagnosing disease that involve measuring a physical property of a part of the body. A change in such a physical property can signal the presence of disease. For example, x-ray techniques measure tissue physical density, ultrasound measures acoustic density, and thermal sensing techniques measures differences in tissue heat generation and conduction. Other properties are electrical, such as the impedance of a body part that is related to the resistance that the body part offers to the flow of electrical current through it.

Values of electrical impedance of various body tissues are well known through studies on intact humans or from excised tissue made available following therapeutic surgical procedures. In addition, it is well documented that a decrease in electrical impedance occurs in tissue as it undergoes cancerous changes. This finding is consistent over many animal species and tissue types, including, for example human breast cancers.

There have been a number of reports of attempts to detect breast tumors using electrical impedance imaging, such as, for example, U.S. Pat. No. 4,486,835. However, there are basic problems when trying to construct an image from impedance data. Electric current does not proceed in straight lines or in a single plane; it follows the path of least resistance, which is inevitably irregular and three-dimensional. As a result, the mathematics for constructing the impedance is very complex and requires simplifying assumptions that greatly decrease image fidelity and resolution.

Despite such difficulties, a method that permits comparisons of electrical properties for diagnostic purposes has been developed that involves homologous body parts, i.e., body parts that are substantially similar, such as a left breast and a right breast. In this method, the impedance of a body part of a patient is compared to the impedance of the homologous body part of the same patient. One technique for screening and diagnosing diseased states within the body using electrical impedance is disclosed in U.S. Pat. No. 6,122,544, which is incorporated herein by reference. In this patent, data are obtained from two anatomically homologous body regions, one of which may be affected by disease. Differences in the electrical properties of the two homologous body parts could signal disease. One subset of the data so obtained is processed and analyzed by structuring the data values as elements of an n×n impedance matrix. The matrices can be further characterized by their eigenvalues and eigenvectors. These matrices and/or their eigenvalues and eigenvectors can be subjected to a pattern recognition process to match for known normal or disease matrix or eigenvalue and eigenvectors patterns. The matrices and/or their eigenvalues and eigenvectors derived from each homologous body region can also be compared, respectively, to each other using various analytical methods and then subjected to criteria established for differentiating normal from diseased states.

Published international patent application, PCT/CA01/01788, which is incorporated herein by reference, discloses a breast electrode array for diagnosing the presence of a disease state in a living organism, wherein the electrode array comprises a flexible body, a plurality of flexible arms extending from the body, and a plurality of electrodes provided by the plurality of flexible arms, wherein the electrodes are arranged on the arms to obtain impedance measurements between respective electrodes. In one embodiment, the plurality of flexible arms are spaced around the flexible body and are provided with an electrode pair. In operation, the electrodes are selected so that the impedance data obtained will include elements of an n×n impedance matrix, plus other impedance values that are typically obtained with tetrapolar impedance measurements. Tetrapolar impedance measurements are associated with injecting current between so called current electrodes and measuring a voltage drop between associated electrodes. In a preferred embodiment, the differences between corresponding homologous impedance measurements in the two body parts are compared in a variety of ways that allow the calculation of metrics that can serve to either indicate the presence of disease or localize the disease to a specific breast quadrant or sector. The impedance differences are also displayed graphically, for example in a frontal plane representation of the breast by partitioning the impedance differences into pixel elements throughout the plane.

Despite the attractive features of this method of diagnosing disease in one of a homologous pair of body parts, there are some problems associated with this straightforward implementation. In particular, the current path through the body part, whether healthy or not, as the current flows from one electrode to the other is, in general, complex. It encompasses to a certain extent, all areas of the body part. In the aforementioned method, this complexity is addressed by simplifying assumptions. This simplification may affect the ability of the method to detect the disease.

SUMMARY OF THE INVENTION

The present invention is directed to an improved method for detecting and diagnosing disease states in a living organism by using a set of electrical impedance measurements. The method is based on the realistic distribution of electric current in the body part. For each impedance measurement, the approximate current distribution is obtained by a numerical computation using a representation of a body part structure, or by the direct measurement performed on a physical model or a control subject's body part. This obtained current distribution is further used to correlate impedances obtained by direct measurements to different areas in the body part.

To achieve this goal, the subject body part is subdivided into a number of small regions called finite elements. For each of the elements and for each of the electrode pairs used to inject current into the body part, a weight factor (obtained by computing or measuring the current density in the element), reflecting the position of the element within the body part, is calculated and stored. Each element has one weight factor for each current injection. Larger weight factors are associated with current injections that result in larger current densities in a particular element. Thus, current injecting scenarios associated with larger weights at a particular element are given greater consideration when detecting disease. The weights are typically calculated or measured with the assumption that there is no disease present. At the same time, baseline impedances associated with each of the current injections are obtained. The weights and baseline impedances for each of the current injection scenarios are stored in the database and used when a diagnosis is made following the measurement of the actual impedances of the subject's body part. For each element, the diagnostic is the sum over all current injections of weight multiplied by the ratio of baseline to measured impedance. This sum is referred to as a Weighted Element Value (WEVal). The higher the value of the sum is, the higher is the probability of the disease at the location of a particular element. Elements are grouped according to known physical characteristics and a sum for each of the groups is obtained. Comparing sums of homologous regions may point to a presence of disease in the body part.

In particular, a system and method for diagnosing the possibility of disease in a body part is described herein. The system includes an electrode array by which an electrical property of the body part may be measured, such as a measured impedance. The system further includes a grid module for representing the body part with a grid having a plurality of finite elements, and for obtaining a baseline electrical property using a model of the body part, such as a baseline impedance. The system also includes a weight module for using the model of the body part to compute a set of weights associated with a particular one of the plurality of finite elements, each weight in the set derived from a particular current injection electrode pair selection. A diagnostic module computes a diagnostic at the particular finite element to diagnose the possibility of disease in the body part, the diagnostic being a function of the measured electrical property, the baseline electrical property and the set of weights.

When quadrupole, instead of bipolar, measurements are performed to obtain the diagnostic, errors may arise because the current electrodes do not coincide with the voltage electrodes. An approach that distinguishes between the two pairs of electrodes is also described below that improves the accuracy of the results. In this approach, the concept of a lead field and the related notion of a sensitivity index (or sensitivity for short) are considered.

In one aspect of the invention a method for obtaining a representation of a part of the human body in the form of an electrical network is disclosed, the method comprising representing the body part with a grid having a plurality of finite elements, the grid contained within a volume, dividing the volume into a plurality of voxels, obtaining a set of weights associated with a particular one of the voxels using a model of the body part, and computing a diagnostic at the particular voxel, the diagnostic being a function of the set of weights, and a measured electrical property obtained with an electrode array.

In another aspect of the invention a method for diagnosing the possibility of disease in a body part is disclosed, the method comprising representing the body part with a grid having a plurality of finite elements, the grid contained within a volume, dividing the volume into a plurality of voxels, obtaining a set of weights associated with a particular one of the voxels using a model of the body part, computing a diagnostic at the particular voxel, the diagnostic being a function of the set of weights, and a measured electrical property obtained with an electrode array, and utilizing the diagnostic to diagnose the possibility of disease in the body part.

Moreover, the methods of the invention further comprise obtaining a baseline electrical property associated with the body part using the model thereof, wherein the diagnostic is a function of the baseline electrical property, the set of weights, and the measured electrical property obtained with the electrode array. Further, the measured electrical property can be conditioned to compute the diagnostic. Moreover, the measured electrical property is an impedance. The baseline electrical property can be obtained using a physical model of the body part. Moreover, the baseline electrical property can be obtained using a control subject. The baseline electrical property can be obtained using a finite element method. In addition, the baseline electrical property can be obtained by obtaining a baseline voltage, and using the baseline voltage to compute a baseline impedance. In the step of obtaining a baseline electrical property, the model of the body part assumes a non-uniform resistivity.

The methods further comprise applying a plurality of electrodes to the body part, and obtaining a measured electrical property of the body part with the plurality of electrodes. The step of applying includes applying $n_{CI}$ current injection electrode pairs on the body part, where $n_{CI}$ is an integer greater than zero, and applying $n_{CI}$ voltage measurement electrode pairs on the body part, each of the current injection electrode pairs associated with one of the $n_{CI}$ voltage measurement electrode pairs.

The step of obtaining a measured electrical property includes injecting a first current between a first pair of the $n_{CI}$ current injection electrode pairs, measuring the resultant voltage difference $V_1^M$ between the voltage measurement electrode pair associated with the first current injection electrode pair, repeating the preceding two steps of injecting and measuring with the other electrode pairs until all $n_{CI}$ voltage differences, $\{V_1^M, V_2^M, \ldots, V_{n_{CI}}^M\}$ are obtained, and using the $n_{CI}$ voltage differences to obtain associated measured impedances, $\{Z_1^M, Z_2^M, \ldots, Z_{n_{CI}}^M\}$, where $Z_j^M$ is the measured impedance obtained by using the $j^{th}$ current injection electrode pair and the voltage measurement electrode pair associated therewith.

If the particular voxel is identified as the $k^{th}$ voxel and the set of weights is denoted by $\{w_{1k}, w_{2k}, \ldots, w_{n_{CI}k}\}$ where $w_{ik}$ is the weight associated with the $k^{th}$ voxel and $i^{th}$ current injection electrode pair, then the step of obtaining a set of weights, includes computing $\nabla V_{i,a}$, the gradient of the electric potential arising when conditions are employed corresponding to injection of current between the ith pair of current injection electrodes, computing $\nabla V_{i,b}$, the gradient of the electric potential arising when conditions are employed corresponding to injection of current between the pair of voltage electrodes associated with the ith pair of current injection electrodes, obtaining a set of sensitivities, $\{\Delta u_{1k}, \Delta u_{2k}, \ldots, \Delta u_{n_{CI}k}\}$, where $\Delta u_{ik}$ is the sensitivity at the $k^{th}$ voxel obtained from $\nabla V_{i,a}$ and $\nabla V_{i,b}$, and obtaining the set of weights using the relation $$w_{ik} = \frac{\Delta u_{ik}}{\sum_{j=1}^{n_{CI}} \Delta u_{jk}}.$$

In the step of obtaining a set of sensitivities, $\Delta u_{ik}$, in some embodiments is given by $$\Delta u_{ik} = -\int_{R_k} \int \int \Delta \kappa_{R_i} \nabla V_{ia} \cdot \nabla V_{ib} dv,$$

where $R_k$ is the volume of the kth voxel, and $\Delta \kappa_{R_k}$ is a deviation of a conductivity at the kth voxel.

The step of obtaining a baseline electrical property includes using the model of the body part to obtain a set of baseline impedances $\{Z_1, Z_2, \ldots, Z_{n_{Cl}}\}$ where $Z_i$ is the impedance associated with the $i^{th}$ electrode pair.

The step of computing a diagnostic includes calculating an average of a function $f(Z_i, Z_i^M)$ at the $k^{th}$ voxel, the average given by $$\langle f_k \rangle = \sum_{i=1}^{n_{Cl}} w_{ik} f(Z_i, Z_i^M),$$

wherein the diagnostic at the $k^{th}$ voxel is defined to be $\langle f_k \rangle$.

In some embodiments, the function $f(Z_i, Z_i^M)$ is given by $$f(Z_i, Z_i^M) = \frac{Z_i}{Z_i^M}.$$

The methods of the invention further comprise obtaining diagnostics at each of the other voxels, wherein the step of utilizing the diagnostic includes averaging the diagnostics at each of the voxels to find an averaged diagnostic $\langle f \rangle$, and calculating a second averaged diagnostic, $\langle f_{homo} \rangle$, corresponding to a homologous body part. The step of utilizing the diagnostic further includes calculating a difference $\langle f \rangle - \langle f_{homo} \rangle$, wherein the quantity $|\langle f \rangle - \langle f_{homo} \rangle|$ is indicative of the possibility of disease in the body part or the homologous body part. Moreover, the step of utilizing the diagnostic further includes calculating a quantity $$\frac{\langle f \rangle - \langle f_{homo} \rangle}{\frac{1}{2}(\langle f \rangle + \langle f_{homo} \rangle)}$$

that is indicative of the possibility of disease in the body part or the homologous body part.

The invention also provides for a system for obtaining a representation of a part of the human body in the form of an electrical network, the system comprising a grid module for representing the body part with a grid having a plurality of finite elements, a voxel module for dividing a volume into a plurality of voxels, the grid being contained by the volume, a weight module for using a model of the body part to compute a set of weights associated with a particular one of the plurality of voxels, and a diagnostic module for computing a diagnostic at the particular voxel to diagnose the possibility of disease in the body part, wherein the diagnostic is a function of the set of weights, and a measured electrical property of the body part obtained with an electrode array.

Further, in another aspect of this invention a system for diagnosing the possibility of disease in a body part is disclosed, the system comprising a grid module for representing the body part with a grid having a plurality of finite elements, a voxel module for dividing a volume into a plurality of voxels, the grid being contained by the volume, a weight module for using a model of the body part to compute a set of weights associated with a particular one of the plurality of voxels, and a diagnostic module for computing a diagnostic at the particular voxel to diagnose the possibility of disease in the body part, wherein the diagnostic is a function of the set of weights, and a measured electrical property of the body part obtained with an electrode array.

In the systems of the invention, the grid module also obtains a baseline electrical property associated with the body part using the model thereof, the diagnostic being a function of the baseline electrical property, the set of weights, and the measured electrical property of the body part obtained with the electrode array. The grid module can also conditions the measured electrical property to compute the diagnostic. The measured electrical property is an impedance. The grid can be two-dimensional in one aspect, and three-dimensional in another aspect. Moreover, the model of the body part is a physical model, and the physical model of the body part can be associated with a control subject. The model of the body part can be a numerical model that can be analyzed using a finite element method. The numerical model assumes a non-uniform resistivity.

Further, the systems of the invention can further comprise an electrode array for obtaining the measured electrical property of the body part. The electrode array can include $n_{Cl}$ current injection electrode pairs to apply on the body part, where $n_{Cl}$ is an integer greater than zero, and $n_{Cl}$ voltage measurement electrode pairs to apply on the body part, each of the current injection electrode pairs associated with one of the $n_{Cl}$ voltage measurement electrode pairs. A first pair of the $n_{Cl}$ current injection electrode pairs transmits a first current through the body part, the voltage measurement electrode pair associated with the first current injection electrode pair measures the resultant voltage difference $V_1^M$, and the other electrode pairs inject and measure to obtain all $n_{Cl}$ voltage differences, $\{V_1^M, V_2^M, \ldots, V_{n_{Cl}}^M\}$.

The systems of the invention can further comprise an impedance measuring instrument for measuring a set of impedance measurements $\{Z_1^M, Z_2^M, \ldots, Z_{n_{Cl}}^M\}$ using the $n_{Cl}$ voltage differences, $Z_i^M$ being the measured impedance associated with the $i^{th}$ voltage electrode pair.

Moreover, the grid module can include a finite element analysis module for computing $\nabla V_{i,a}$, the gradient of the electric potential arising when conditions are employed corresponding to injection of current between the ith pair of current injection electrodes, and for computing $\nabla V_{i,b}$, the gradient of the electric potential arising when conditions are employed corresponding to injection of current between the pair of voltage electrodes associated with the ith pair of current injection electrodes, and a sensitivity module for using the gradients $\nabla V_{i,a}$ and $\nabla V_{i,b}$ within a $k^{th}$ voxel to obtain a set of sensitivities, $\{\Delta u_{1k}, \Delta u_{2k}, \ldots, \Delta u_{n_{Cl}k}\}$, where $\Delta u_{ik}$ is the sensitivity at the $k^{th}$ voxel obtained from $\nabla V_{i,a}$ and $\nabla V_{i,b}$, wherein the set of weights are calculated according to $$w_{ik} = \frac{\Delta u_{ik}}{\sum_{j=1}^{n_{Cl}} \Delta u_{jk}}.$$

The sensitivity module obtains $\Delta u_{ik}$ using the formula $$\Delta u_{ik} = -\int_{R_k} \int \int \Delta \kappa_{R_i} \nabla V_{ia} \cdot \nabla V_{ib} dv,$$

where $R_k$ is the volume of the kth voxel, and $\Delta \kappa_{R_k}$ is a deviation of a conductivity at the kth voxel. The grid module uses the model of the body part to obtain a set of baseline impedances $\{Z_1, Z_2, \ldots, Z_{n_{Cl}}\}$ where $Z_i$ is the impedance associated with the $i^{th}$ electrode pair.

The systems further comprise an averaging module for calculating an average of a function $f(Z_i, Z_i^M)$ at the $k^{th}$ voxel, the average given by $$\langle f_k \rangle = \sum_{i=1}^{n_{Cl}} w_{ik} f(Z_i, Z_i^M),$$

wherein the diagnostic at the $k^{th}$ voxel is defined to be $\langle f_k \rangle$. The function $f(Z_i, Z_i^M)$ is given by $$f(Z_i, Z_i^M) = \frac{Z_i}{Z_i^M}.$$

Moreover, the electrode array, the grid module and the weight module are used to calculate diagnostics at the other voxels, which together with the particular one, comprise the plurality of voxels, and the diagnostic module averages the diagnostics at the voxels to find an averaged diagnostic $\langle f \rangle$, and calculates a second averaged diagnostic, $\langle f_{homo} \rangle$, corresponding to a homologous body part. The diagnostic module calculates a difference $\langle f \rangle - \langle f_{homo} \rangle$ that is indicative of the possibility of disease in the body part or the homologous body part. In particular, the diagnostic module calculates a quantity $$\frac{\langle f \rangle - \langle f_{homo} \rangle}{\frac{1}{2}(\langle f \rangle + \langle f_{homo} \rangle)}$$

that is indicative of the possibility of disease in the body part or the homologous body part.

BRIEF DESCRIPTION OF THE DRAWINGS

FIGS. 6A and 6B are sample WEVal plots of an actual subject that were obtained to detect breast cancer, using a system in accordance with an embodiment of the invention;

DETAILED DESCRIPTION OF THE INVENTION

Figure 1A:
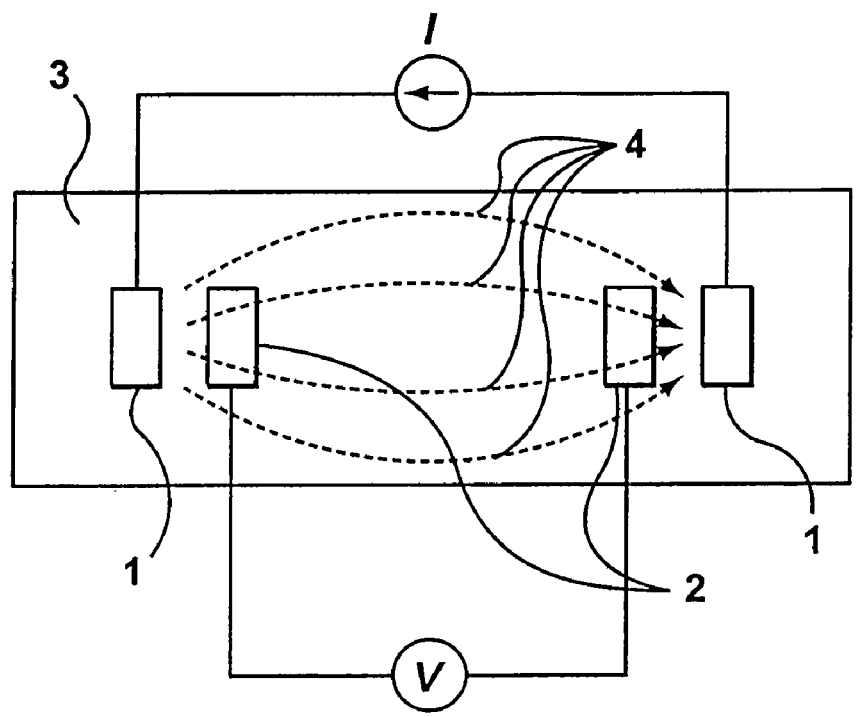
FIG. 1A is a schematic drawing of a basic tetrapolar measurement according to an embodiment of the invention.
Figure 1B:
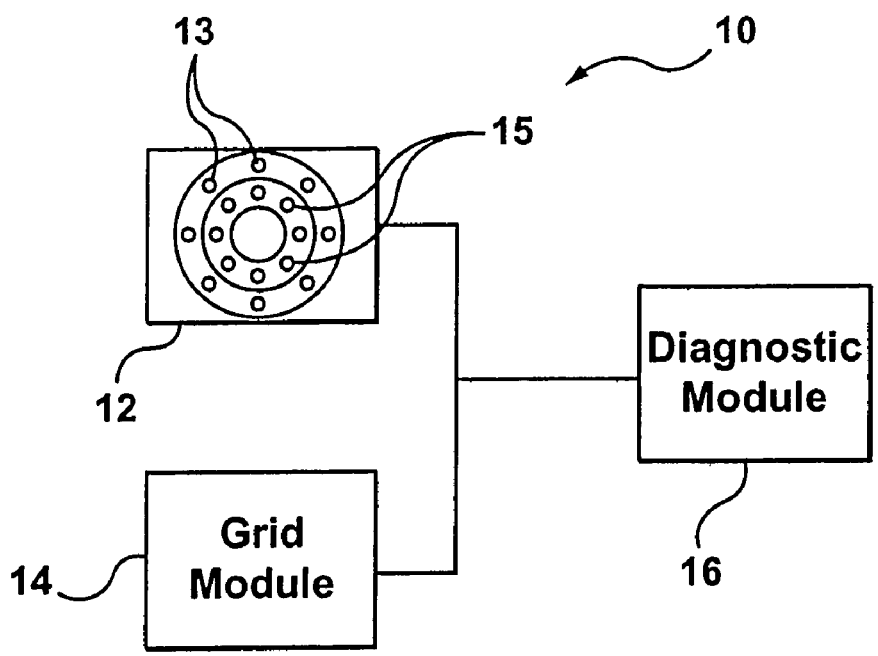
FIG. 1B is a block diagram of a system for detecting and diagnosing disease in a body part in accordance with aspects of the invention.
Figure 1C:
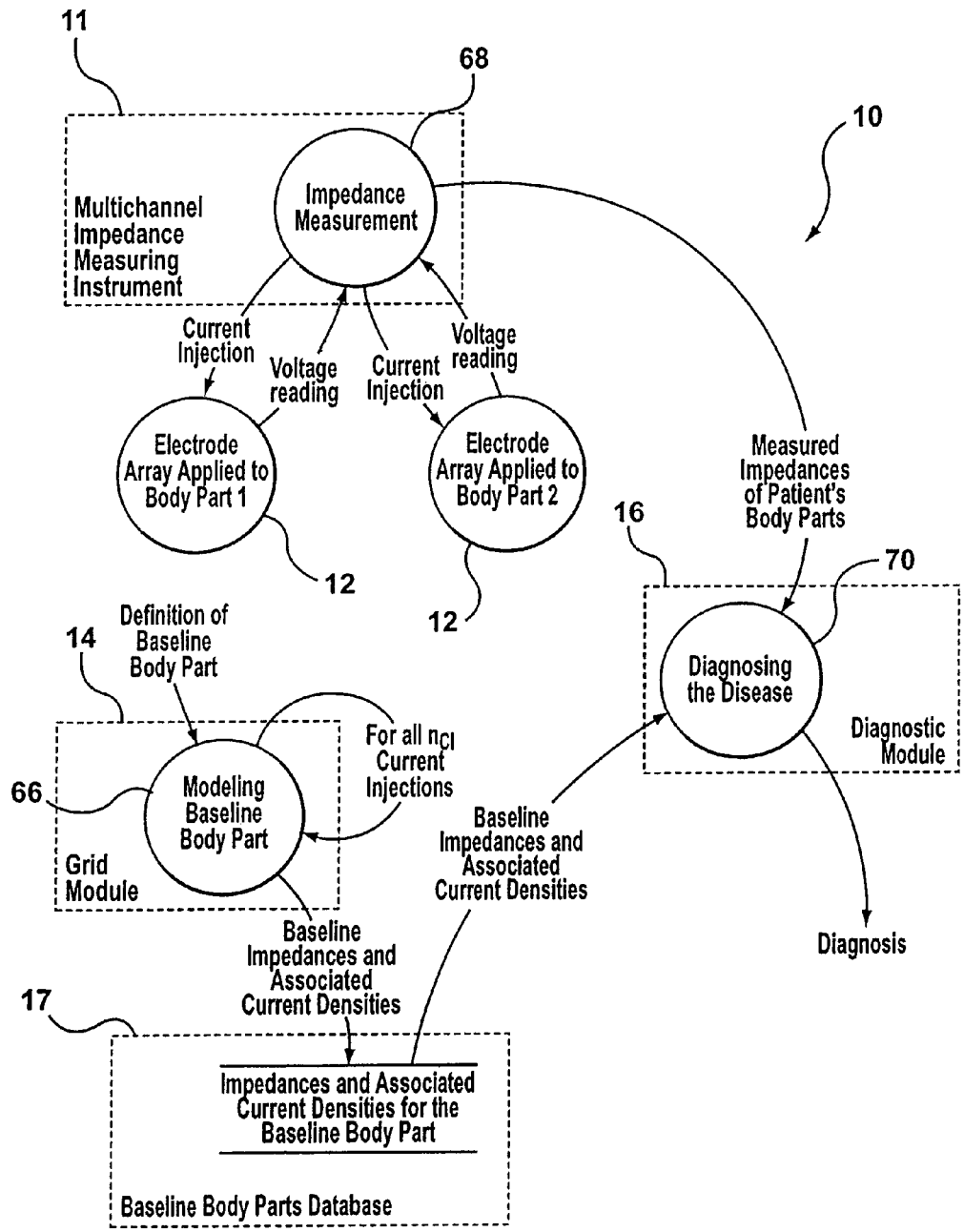
FIG. 1C is a data flow diagram of a method for detecting and diagnosing disease in a body part, in accordance with aspects of the invention.

FIG. 1A shows a schematic of components used to perform a tetrapolar impedance measurement, which measurements are used for detecting and diagnosing disease, as described in more detail below. FIGS. 1B and 1C show a block diagram of a system 10 and an outline of a method for detecting and diagnosing disease in a body part, such as breast cancer. The method uses impedance measurements taken from a multi-channel impedance measuring instrument 11 with a pair of electrode arrays 12, like the one described in PCT/CA01/01788, a grid module 14 and a diagnostic module 16.

Referring to FIG. 1A, a single electrical impedance measurement is performed using four electrodes. One pair of electrodes 1 is used for the application of current I, and the other pair of electrodes 2 is used to measure the voltage V that is produced across a material, such as breast tissue 3, by the current. The current I flowing between electrodes 1 is indicated by the arrows 4. The impedance Z is the ratio of V to I; i.e., Z=V/I. By using separate electrode pairs for current injection and voltage measurement, polarization effects at the voltage measurement electrodes 2 are minimized and a more accurate measurement of impedance can be produced. It should be understood that, in general, the voltage electrodes 2 need not be disposed between the two current electrodes 1.

Impedance consists of two components, resistance and capacitive reactance (or equivalently, the magnitude of impedance and its phase angle). Both components are measured and analyzed in the present invention. However, in examples described below, only resistance is used and interchangeably referred to as either resistance or the more general term impedance.

As has been noted above, by performing tetrapolar measurements in which separate electrode pairs are used for current injection and voltage measurement, polarization effects at the voltage measurement electrodes 2 are minimized and more accurate measurements of impedance can be performed. However, there may be some embodiments in which bipolar, instead of a tetrapolar, measurements can be performed as part of the general method for diagnosing disease discussed below. If bipolar measurements are performed, a correction factor can be used that corrects for the polarization effects arising from skin-to-electrode interface.

FIG. 1B shows a schematic of the electrode array 12. Eight current injection electrodes 13, and eight associated voltage measurement electrodes 15 are shown. In general, there are $n_e$ current injection electrodes and $n_e$ associated voltage measurement electrodes in the electrode array. The electrodes are applied on the body part, each of the current injection electrodes being associated with the adjacent voltage measurement electrode. Impedance is measured between two voltage electrodes when the current is injected between associated current electrodes. Since there are $n_{Cl}=n_e \cdot (n_e-1)/2$ pairs of current injection electrodes, and an equal number of voltage measurement electrode pairs, the total number of independent current injections and related impedances is $n_{Cl}$. It should be understood that the electrode array shown is but one possible electrode array. Other electrode arrays may also be used.

As discussed in more detail below, the grid module 14 uses a numerical or physical model of a baseline (idealized or reference) body part to compute baseline values. In particular, at step (66), baseline impedances and associated gradients for the baseline body part are calculated in the grid module 14. As detailed below, the associated gradients can be used to calculate current densities at each finite element. The baseline impedances for each of the $n_{Cl}$ current injections, and the associated current densities for each of the finite elements and for each of the $n_{CI}$ current injections are stored in a baseline body parts database 17.

At step (68), the impedance is measured $n_{CI}$ times resulting in the set of values, $\{Z_1^M, Z_2^M, \ldots, Z_{n_{CI}}^M\}$, where $Z_j^M$ is the impedance measured between the voltage electrodes associated with the $j^{th}$ current injection electrode pair when current is injected between that current injection electrode pair, as required in tetrapolar impedance measurement.

The grid module 14 includes software and/or hardware for representing the body part with a grid of elements that are so small that the voltage gradient during arbitrary current injection is approximately constant within any single element. For example, if the body part is modeled as a two-dimensional surface, then the grid can be composed of triangles that "tile" the surface. Alternatively, the body part can be modeled by a three-dimensional grid whose elements are tetrahedrons, for example. Each finite element is associated with a plurality of nodes, typically on the perimeter of the finite element. As well, each finite element is characterized by its electrical material property, namely resistivity and/or permittivity. Adjacent elements share the nodes associated with the common side or face. When the elements are small enough to ensure that the current density throughout the element is constant for each of the current injections, the voltage gradient throughout the element is also constant and proportional to the current density.

The grid module 14 also includes software and/or hardware for deriving the current density for each of the elements in the grid. It does this by calculating the current density using a numerical or physical model, or by using population study information, as discussed in more detail below.

The diagnostic module 16 includes software and/or hardware for detecting the presence of a tumor in the body part at step (70). As described in more detail below, the diagnosis is based on a diagnostic that is a function of the impedance measurements obtained from a subject using the impedance measuring instrument 11, and a weighting factor derived from the estimated value of the current density throughout the body part, obtained using grid module 14.

Figure 2:
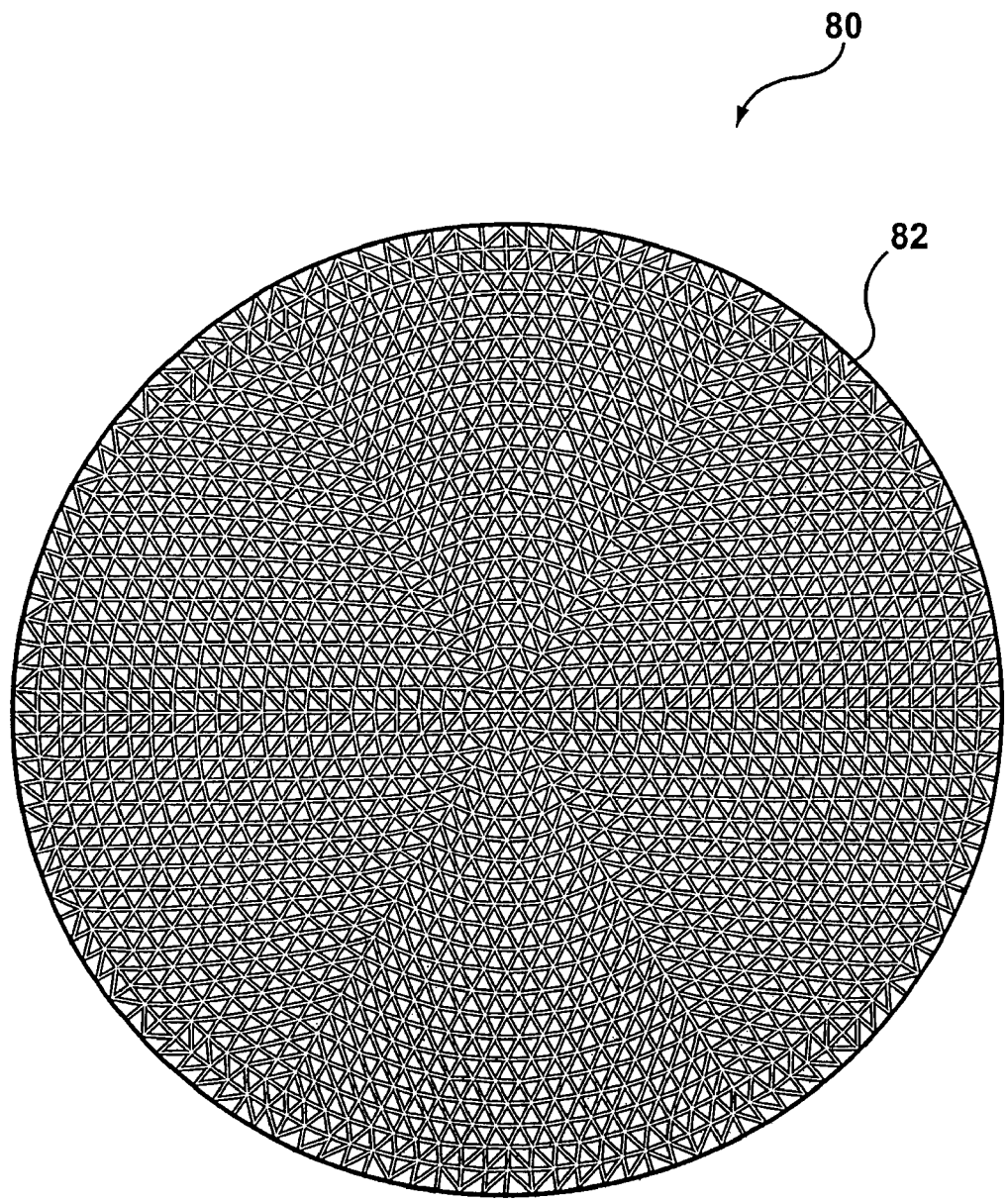
FIG. 2 is a sample finite element grid produced by the grid module of FIG. 1B, the grid representing a body part that can be used to calculate baseline electrical properties.

FIG. 2 shows a representation of the baseline body part divided into a grid 80 composed of a plurality of finite elements 82. Once the body part is subdivided using grid module 14 into a number of finite elements 82, there are several methods that can be used to calculate baseline values, such as the current density associated with a particular current injection and with a particular finite element 82 of the grid 80. FIG. 2 shows one embodiment of the present invention in which several thousand finite elements 82 are used, as required to justify linearizing the equations used to numerically compute the relevant electrical properties.

The preferred method used by the grid module 14 to associate a voltage gradient with a particular finite element 82 is a numerical finite element method that assumes that the resistivity of the body part is uniform. The method numerically solves Laplace's equation, known to those of ordinary skill, to compute the electric potential at the nodes of the finite element grid from which the electric voltage gradient can be obtained. Due to uniform resistivity, current density is proportional to the voltage gradient everywhere in the body part.

A second method that can be used by the grid module 14 is related to the last method, except that instead of assuming a uniform resistivity, more realistic resistivities and/or permittivities can be used that reflect the known internal structure of the body part. In this case the current density is proportional to the electric voltage gradient in each of the elements, but the voltage gradient to current density ratio depends on the resistivity and/or reactivity associated with the particular finite element 82.

The third method involves using a physical model of a typical breast. This typical breast acts as a baseline representation of the body part. The model is designed so that the measured impedance matrix is close to the average impedance matrix for the normal subject with the body part of the particular size. Each finite element 82 obtained using the grid module 14 is associated with the particular location (x, y and z coordinates) in the physical model. The current density at each of the finite elements 82 and for each of the current injections is obtained using one of the available instruments for measuring the current density. The current density instrument, for example, can be combined with magnetic resonance imaging (MRI) to measure and display the current density superimposed on the MRI image at any location of the body part model.

The fourth method is similar to the third method except that the measurement of the current density for each current injection and at the location of each of the finite elements 82 defined by the grid module 14 is performed on the body part of an actual control subject. For example, the same combination of instruments as above can be used to measure and display the current density superimposed on the MRI image at any location in the actual body part.

Figure 3:
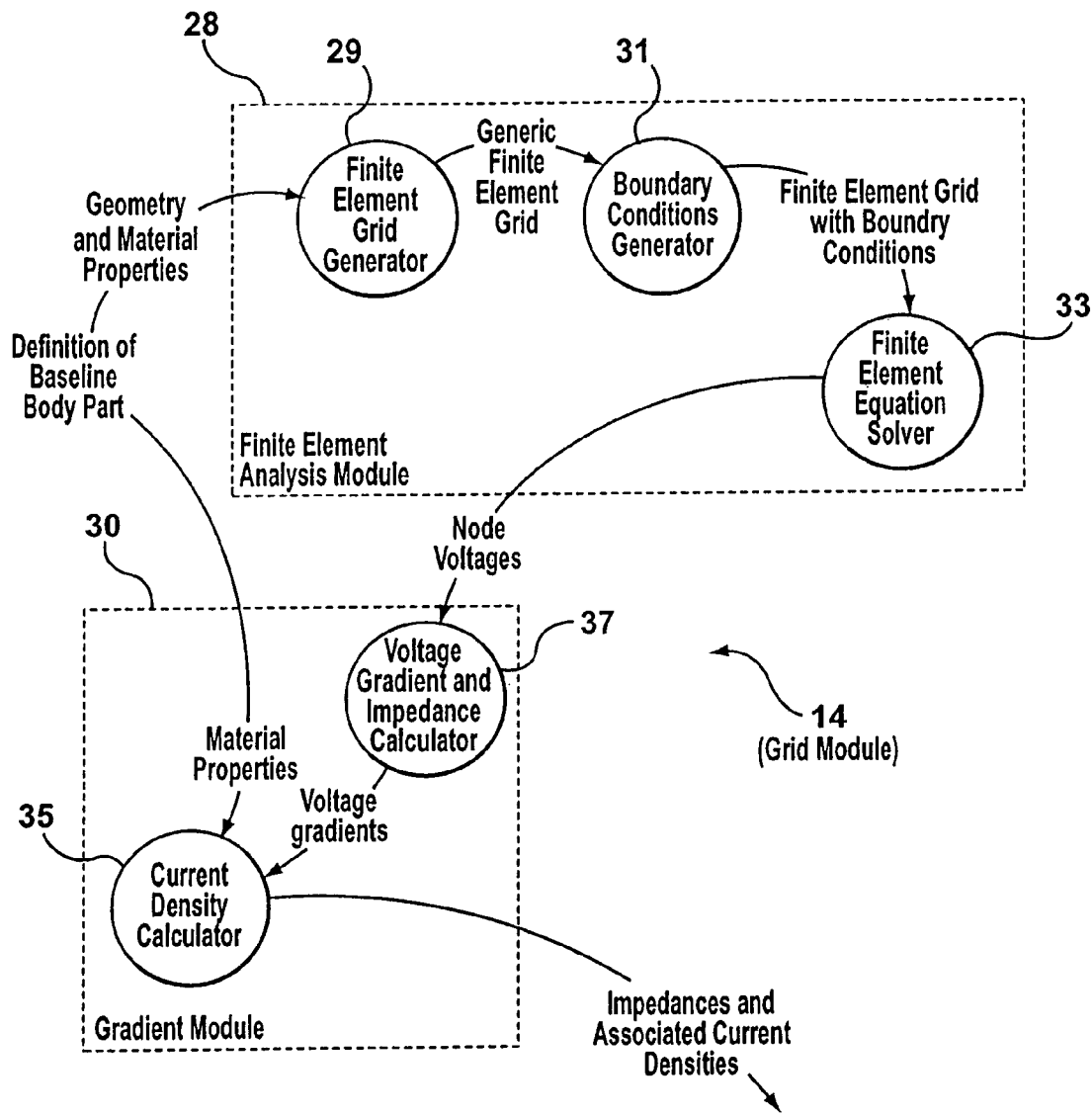
FIG. 3 is a data flow diagram of the grid module of FIG. 1B, in one embodiment of the present invention that employs a numerical finite element method.

FIG. 3 shows a block data flow diagram of the grid module 14 in the preferred embodiment of the invention where it includes a finite element analysis module 28 and a gradient module 30.

In the preferred embodiment of the invention, for any single current injection, a finite element method is used to estimate baseline values for electric potential gradients and resulting current densities in each of the elements. In addition, the grid module 14 uses the finite element method to compute the baseline impedance. More generally, the baseline impedance refers to the impedance calculated by the grid module 14 (denoted by $Z_j$, for the $j^{th}$ electrode pair) using an appropriate physical or numerical model, as distinguished from the measured impedance, $Z_j^M$, obtained by a measurement on a subject using an electrode array.

The finite element analysis module 28 includes hardware and/or software that employs various boundary conditions, corresponding to the injections of current between the various pairs of current injection electrodes 13 (FIG. 1B), to compute the electric potential at all the nodes in the grid. The node voltage $V_{ji}$ is the voltage that arises at the node j when a current injection i is applied, where the $i^{th}$ current injection refers to the injection of current between the $i^{th}$ current injection electrode pair.

Specifically, the finite element analysis module 28 includes a finite element grid generator 29, a boundary conditions generator 31 and a finite element equation solver 33. The finite element grid generator 29 generates a grid 80 of finite elements 82 that spans a representation of the body part. Position on the representation of the body part can be discretized if each finite element is associated with several nodes, typically on the perimeter of the finite element.

To compute the potential, V, as a function of position on the grid, Laplace's equation $\nabla^2 V = 0$ is solved using a numerical finite element method. The boundary conditions generator 31 assigns boundary conditions corresponding to the various $n_{CI}$ current injections. The finite element equation solver 33 employs the numerical finite element method for solving Laplace's equation. Many different types of such methods can be used, such as a Lax differencing scheme for solving partial differential equations. Several other techniques known to those of ordinary skill in the art can be utilized.

In addition to finding the electric potential as a function of node position, the grid module 14 also finds voltage differences between voltage measurement electrodes 15. In particular, using boundary conditions corresponding to the current injected by the first pair of current injection electrodes yields $V_1$, the voltage drops between the first pair of voltage measurement electrodes. Using boundary conditions corresponding to the current injected by the second pair of current injection electrodes yields $V_2$, the voltage drop between the second pair of voltage measurement electrodes. Continuing in this manner yields all $n_{CI}$ voltages $\{V_1, V_2, \ldots, V_{n_{CI}}\}$. Each time Laplace's equation is solved, the finite element method yields the potential at every node of the grid as well. The node voltage $V_{ji}$ is the voltage that arises at the node j when a current injection i is applied. The gradient module 30 utilizes the calculated node voltages to find an estimated current density at the element k for the current injection i, $J_{ik}$. The grid module 14 similarly obtains all $n_{CI}$ impedances $\{Z_1, Z_2, \ldots, Z_{n_{CI}}\}$ and all the current densities $\{J_{1k}, J_{2k}, \ldots J_{n_{CI}k}\}$, at the finite element k. In particular, to obtain $J_{ik}$, where $J_{ik}$ is the magnitude of the current density in the $k^{th}$ finite element for the current injection i, the gradient module 30 uses the electric potential at each node associated with finite element k. To this end, the magnitude of the gradient of the electric potential, which is equal to the magnitude of the electric field, is first obtained by a voltage gradient calculator 37.

For example, supposing the element to be two dimensional with potential $V=\phi(x,y)$, then $E=|\nabla\phi|$ where E is the magnitude of the electric field. The voltage gradient calculator 37 can obtain E as follows. In the (x,y,V) coordinate system, if $\theta$ is the angle between $\hat{k}$, the unit normal in the V direction, and the perpendicular to the surface $V=\phi(x,y)$, then $\tan\theta=|\nabla\phi|$. To see this, an auxiliary function $F(x,y,V)=V-\phi(x,y)$ can be introduced. The quantity $\nabla F/|\nabla F|$ is a normal vector perpendicular to the level surface $F(x,y,V)=$const., or, with const=0, a normal vector perpendicular to the surface $V=\phi(x,y)$. Then, $$\frac{\sin\theta}{\cos\theta} = \frac{\left|\hat{k} \times \frac{\nabla V}{|\nabla V|}\right|}{\hat{k} \cdot \frac{\nabla V}{|\nabla V|}}$$

$$= \left[\left(\frac{\partial\phi}{\partial x}\right)^2 + \left(\frac{\partial\phi}{\partial y}\right)^2\right]^{1/2}$$

$$= |\nabla\phi|$$

$$= E$$

when employing the finite element analysis, the finite element analysis module 28 can either assume the body part to have a uniform resistance and/or reactance, or the resistance and/or reactance can be taken to be non-uniform to reflect the known structure of the body part.

A current density calculator 35 calculates the magnitude of the current density J from the magnitude of the electric field E and the tissue resistivity $\rho$ using the microscopic version of Ohm's Law stating that at every point, $J=E/\rho$.

Figure 4:
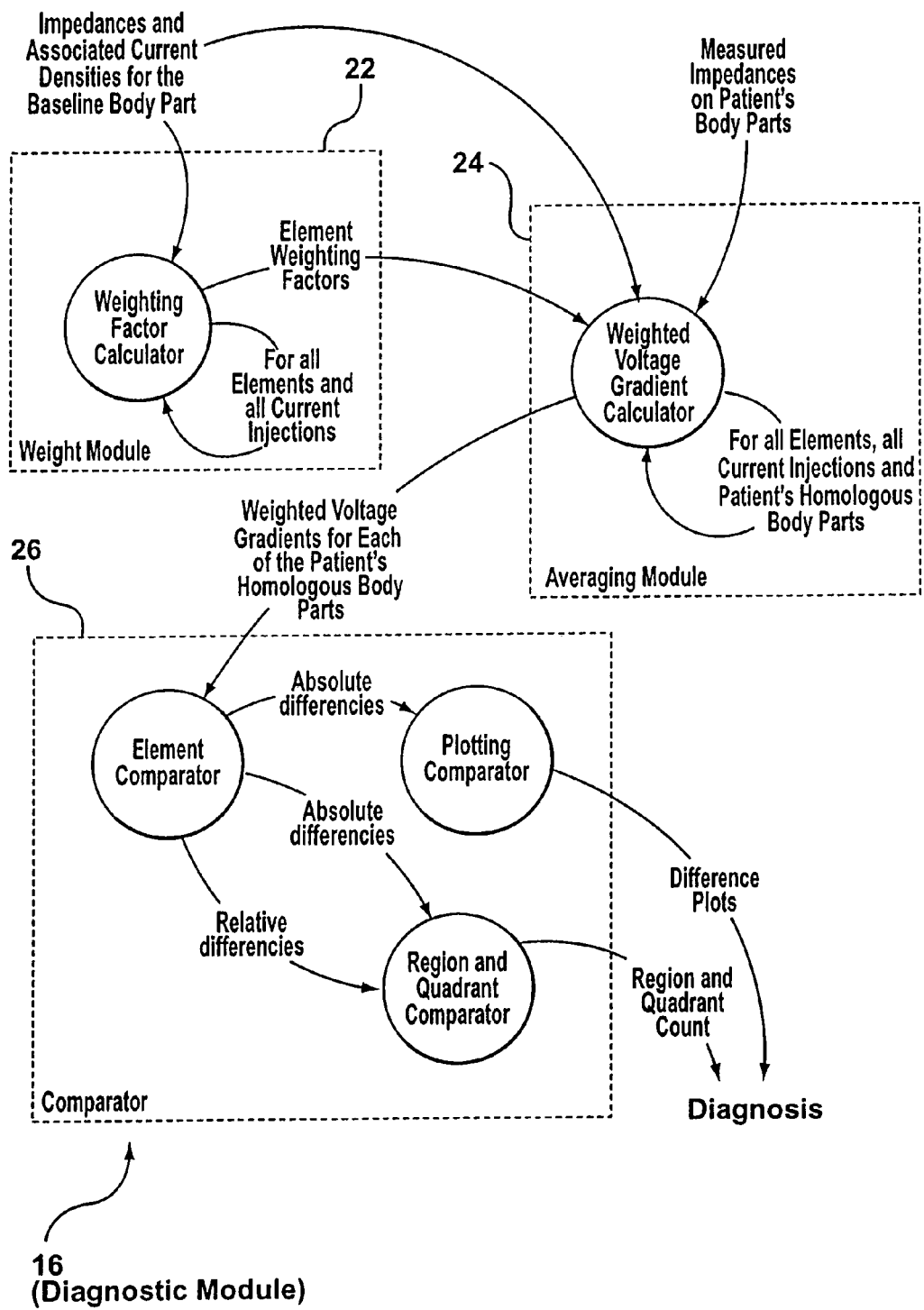
FIG. 4 is a data flow diagram of the diagnostic module of FIG. 1B, in one embodiment of the present invention.

FIG. 4 shows a block data flow diagram of the diagnostic module 16 of FIG. 1B, in one embodiment of the present invention. The diagnostic module 16 includes a weight module 22, an averaging module 24 and a comparator 26.

As discussed previously, the diagnostic module 16 computes a Weighted Element Value (WEVal) parameter (diagnostic) at each of the finite elements 82 of the grid 80 representing the body part, and utilizes the diagnostic to diagnose the possibility of disease in the body part. The diagnostic is a function of the impedances and current densities calculated and/or measured for the baseline body part and impedances measured on the body part of the subject.

The weight module 22 includes software and/or hardware for calculating weights for the element k and the current injection i, $w_{ik}$, given by $$w_{ik} = \frac{J_{ik}}{\sum_{j=1}^{n_{CI}} J_{jk}}.$$

The quantity $J_{1k}$ is the magnitude of the current density, which exists at the finite element k when the reference current is applied between the first pair of current injection electrodes. The quantity $J_{2k}$ is the magnitude of the current density, which exists at the finite element k when the reference current is applied between the second pair of current injection electrodes, and so on.

The averaging module 24 includes software and/or hardware for calculating a weighted average of a function $f(Z_i, Z_i^M)$. The diagnostic at the finite element k is defined to be $$\langle f_k \rangle = \sum_{i=1}^{n_{CI}} w_{ik} f(Z_i, Z_i^M).$$

The diagnostic $\langle f_k \rangle$ is referred to as the Weighted Element Value (WEVal). The quantity $Z_1$ is the impedance between the first pair of electrodes for the baseline body part. The quantity $Z_2$ is the impedance between the second pair of electrodes for the baseline body part, and so on. The $Z_i$ can be obtained using a numerical calculation or using a physical model (an artificial reproduction or the real body part of a control subject). The $Z_i^M$ are obtained by direct measurement on the body part of a subject using an electrode array. In the preferred embodiment of the present invention, the function $f(Z_i, Z_i^M)$ is $$f(Z_i, Z_i^M) = \frac{Z_i}{Z_i^M}.$$

It should be understood that other functions $f$ might be used in other embodiments, including functions that are independent of the baseline values $Z_i$. It should be further understood that the diagnostic module 16 can condition the raw measurements $Z_i^M$, such as by standardizing with a factor, etc, to find the diagnostic. Thus, in one embodiment, the function can be given by $$f(Z_i, Z_i^M) = \frac{Z_i}{\alpha Z_i^M}$$

for some appropriate factor, $\alpha$, used to condition the raw data, which conditioned data may be used to compute the diagnostic.

for some appropriate factor, $\alpha$, used to condition the raw data, which conditioned data may be used to compute the diagnostic.

In a human subject, some body parts have homology in the body. For example, in females, the right breast has a homolog, namely the left breast. In a preferred embodiment of the invention, $\langle f_k \rangle$ is averaged over all the finite elements of the right breast to yield $\langle f_{right} \rangle$, and all the finite elements of the left breast to yield $\langle f_{left} \rangle$. In a different embodiment, $\langle f_{right} \rangle$ can refer to an average over finite elements belonging to a particular region within the right breast.

More generally, if the N finite elements comprising the grid are not all of equal size, the average is given by $$\langle f_{right} \rangle = \sum_{k=1}^{N} p_k \langle f_k \rangle,$$

where the probabilities $p_k$ are given by $$p_k = \chi_A(k) V_k / V_A.$$

In this last expression, $\chi_A(k)$ is the characteristic function for a region A of the body part:

$$\chi_A(k) = \begin{cases} 1, & \text{if finite element } k \subset A \\ 0, & \text{otherwise} \end{cases}$$

and $V_k$ and $V_A$ are the volumes (if the grid is three dimensional) or the areas (if the grid is two-dimensional) of finite element k and region A, respectively.

The measured impedances in the body part are expected to be somewhat different from the values measured in the homologous body part. However, these differences are expected to be more pronounced if only one of these body parts contains a malignant tumor.

The comparator 26 includes hardware and/or software for comparing $\langle f_{left} \rangle$ to $\langle f_{right} \rangle$ to diagnose the possibility of disease. For example, if breast cancer is being diagnosed and if it is assumed that at least one breast is non-cancerous, then a difference between $\langle f_{left} \rangle$ and $\langle f_{right} \rangle$ may be due to a change in the electrical properties of one breast brought about by the presence of a cancer.

The comparator 26 calculates the absolute difference $|\langle f_{right} \rangle - \langle f_{left} \rangle|$ or a relative difference such as $$(\langle f_{right} \rangle - \langle f_{left} \rangle) / \left[ \frac{1}{2} \cdot (\langle f_{right} \rangle + \langle f_{left} \rangle) \right]$$

that is indicative of the possibility of disease in the body part or the homologous body part. Where there is a significant difference, further analysis can be performed to discern which of the homologous pairs may be cancerous. For example, as described above, it is known that the electrical properties of cancerous tissue deviate from the norm in a predictable way. Thus, the body part having electrical properties more like those of a cancerous body part can be suspect.

It should be understood that the principles of the present invention can be applied to diagnose disease in a body part without comparison to a homolog. For example, the diagnostic WEVal can be compared to a population average, to the baseline value, or to some other standard to diagnose disease.

Figure 5:
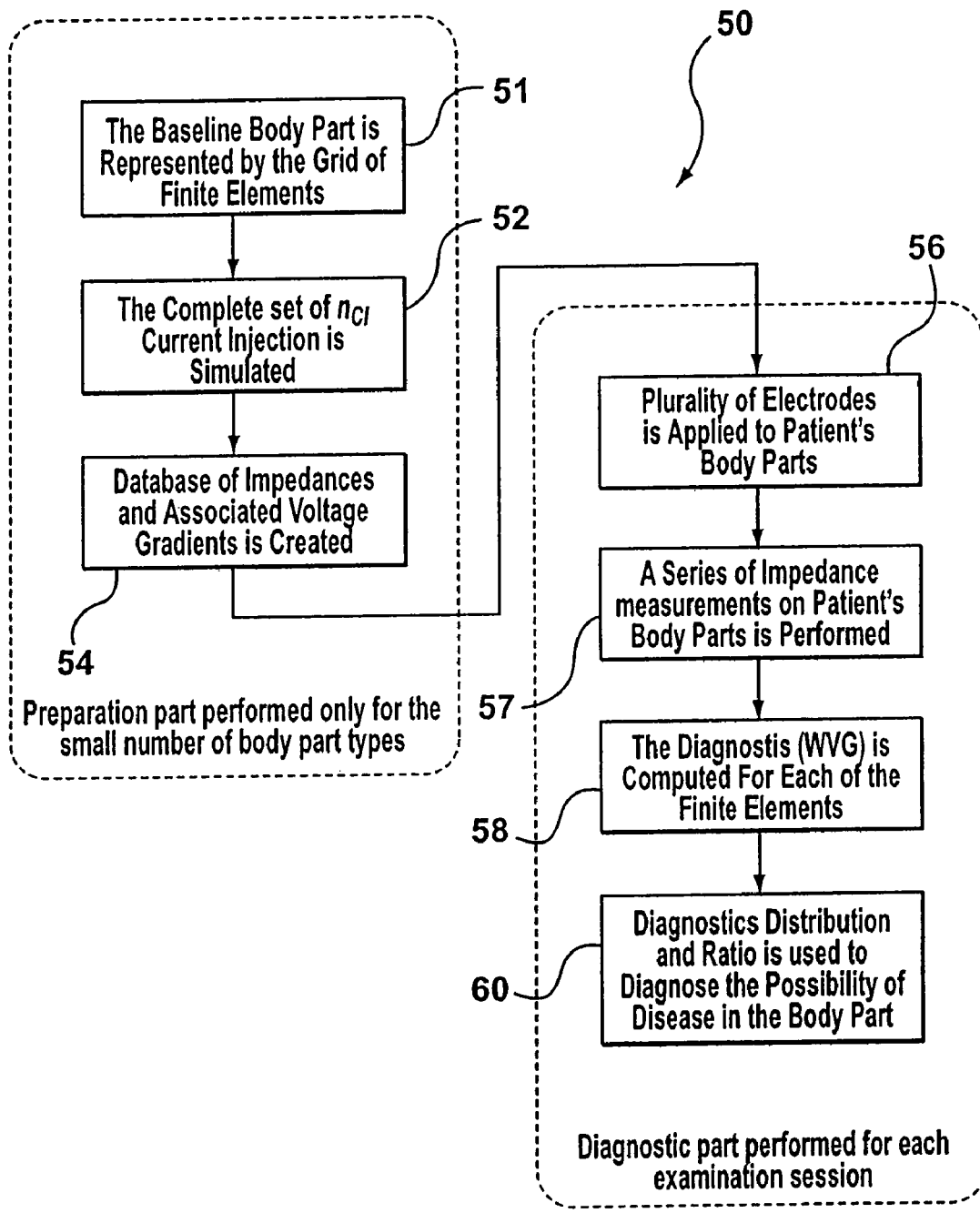
FIG. 5 is a flowchart illustrating the method steps performed by the diagnostic system of FIG. 1B to diagnose disease in accordance with aspects of the invention.

FIG. 5 shows a flowchart that illustrates the main steps 50 utilized by system 10 to diagnose the possibility of disease in a body part. The first part of the procedure is preparatory and establishes standard or idealized baselines for a typical body part and results are stored in the database to be used as a reference for numerous subjects. At step (51), the baseline body part is represented with a grid of finite elements. The grid can be two-dimensional, or three-dimensional. Next, at step (52), $n_{CI}$ current injections are simulated to yield a database (54) of impedances and associated voltage gradients. These steps may be repeated to collect several typical sets of data depending on the size, body fat, or some other characteristic of the subject or the body part. This concludes the preparatory part. The subject-specific part of the procedure is described next. At step (56) a plurality of electrodes is applied to the body part, such as a breast and, at step (57), the plurality of electrodes measure impedance of the body part between electrode pairs. At step (58), a diagnostic is computed at each of the finite elements, the diagnostic being a function of the measured impedance and the values of impedance and gradients from the database. Subsequently, at step (60), the diagnostic is utilized to diagnose the possibility of disease in the body part.

Referring to FIGS. 6A and 6B, sample results in the form of two gray scale plots are shown illustrating the value of the system and method of the present invention in diagnosing breast cancer. In FIGS. 6A and 6B, the right breast 72 and the left breast 74 are represented in the frontal plane as two circular plots, with darkness of gray increasing as the homologous difference of the diagnostic becomes more profound. This patient had an invasive ductal adenocarcinoma in the mid outer right breast. To generate these circular plots, each breast was represented by a circle with a 2D grid of finite elements. In FIGS. 6A and 6B, the finite elements comprising the grid are not shown.

The quantity $|\langle f_{right} \rangle - \langle f_{left} \rangle|$ as calculated by the comparator 26 for homologous elements is, by convention, plotted on the side having the larger WEVal; i.e., on the right breast for elements where $\langle f_{right} \rangle > \langle f_{left} \rangle$ (FIG. 6A) and on the left breast where $\langle f_{left} \rangle > \langle f_{right} \rangle$ (FIG. 6B). These differences are scaled in the figure to the maximum level of black. Sixteen different levels of gray are presented, and some contrasting has been added to emphasize areas where the differences are highest. However, none of these scaling methods appreciably influenced the results. As can be seen in FIG. 6B, the shading in the normal left breast 74 is uniform (the light-most shade), indicating that for this subject $\langle f_{right} \rangle > \langle f_{left} \rangle$ everywhere.

When quadrupole, instead of bipolar, measurements are performed to obtain the diagnostic, errors may arise because the current electrodes do not coincide with the voltage electrodes. A somewhat modified approach to that described above may be employed that distinguishes between the two pairs of electrodes and by so doing improves the accuracy of the results. In this modified approach, the concept of a lead field and the related notion of a sensitivity index (or sensitivity for short) are considered. In The voltage across the lead b for a unit current injection over lead a is then:

$$u_{a,b} = \frac{\iint_{\beta_2} V_b \, ds}{\iint_{\beta_2} 1 \cdot ds} - \frac{\iint_{\beta_1} V_a \, ds}{\iint_{\beta_1} 1 \cdot ds}$$

As shown in the Appendix below, this last expression may be further simplified:

$$u_{a,b} = \iiint_B \kappa \nabla V_a \cdot \nabla V_b \, dv.$$

The Geselowitz-Lehr Sensitivity Relationship is defined as:

$$-\int\int\int_B \Delta\kappa \nabla V_a \cdot \nabla V_b \, dv$$

where $V_a$ and $V_b$ are the voltage fields generated across leads a and b respectively, for a constant conductivity $\kappa_c$, $\Delta\kappa$ is the deviation of the actual conductivity from the constant conductivity, and $\Delta u_{a,b}$ is the expected deviation of the voltage reading across the lead b for a unit current injection over lead a. The change in $V_a$ is assumed small compared to the change in $\kappa$.

As above for the current densities, several models can be used to obtain the sensitivities. In particular, a numerical finite element method that assumes that the resistivity of the body part is uniform can be used. The method numerically solves Laplace's equation, known to those of ordinary skill, to compute the electric potential at the nodes of a finite element grid from which the electric voltage gradient can be obtained.

A second model that can be used to obtain the sensitivities is similar to the last one, except that instead of assuming a uniform resistivity, more realistic resistivities and/or permittivities can be used that reflect the known internal structure of the body part.

The third approach involves using a physical model of a typical breast. This typical breast acts as a baseline representation of the body part. The model is designed so that the measured impedance matrix is close to the average impedance matrix for the normal subject with the body part of the particular size.

The fourth model is similar to the third except that measurement of sensitivities is performed on the body part of an actual control subject.

In what follows, emphasis is placed on the numerical models employing finite element analysis, but it should be understood that physical models (artificial or real) can also be used to obtain the sensitivities.

Figure 7:
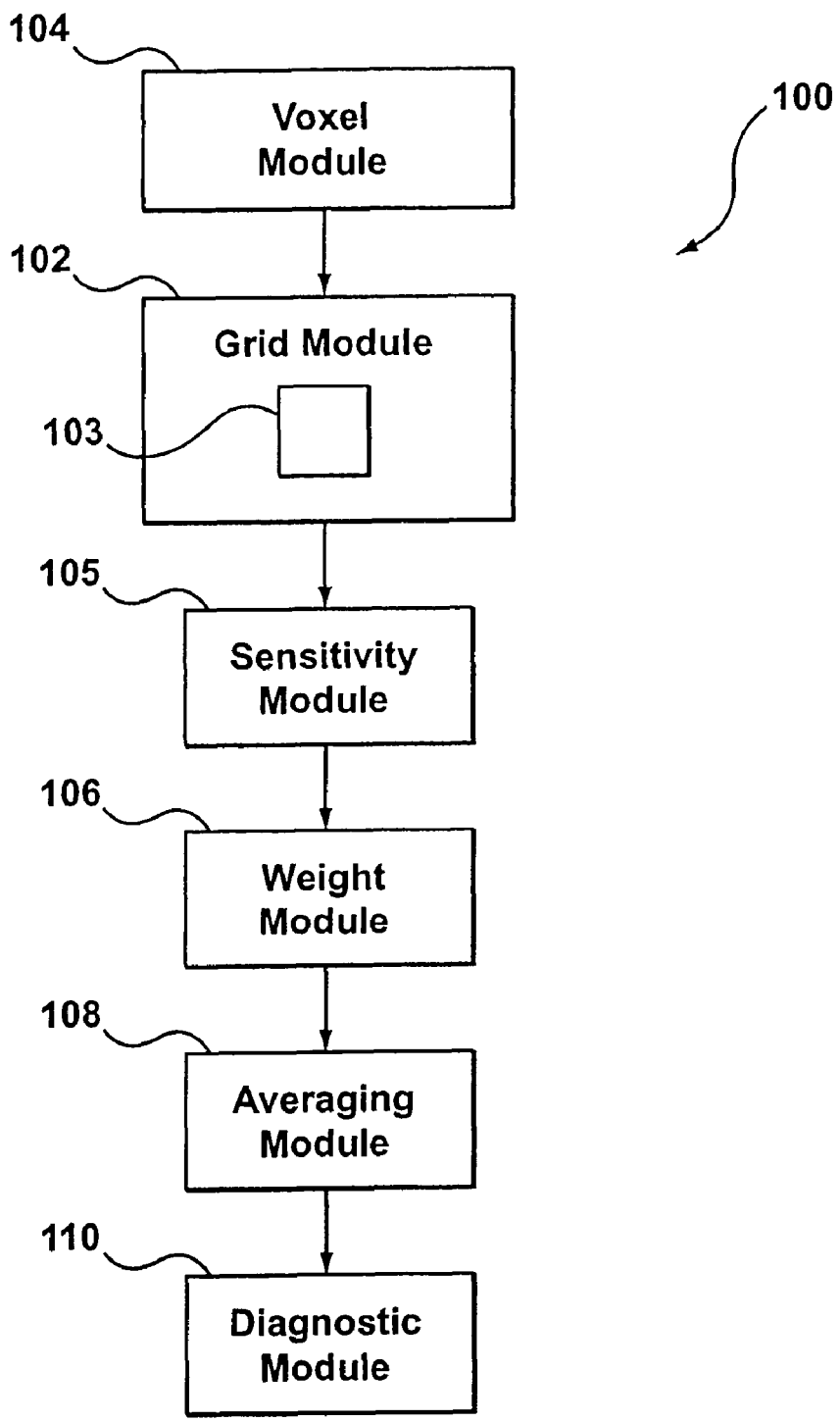
FIG. 7 is a block diagram of a system for diagnosing the possibility of disease in a body part in accordance with an embodiment of the invention.

FIG. 7 shows a block diagram of a system 100 for diagnosing the possibility of disease in a body part using a sensitivity. The system 100 includes a grid module 102 for representing the body part with a grid having a plurality of finite elements. The grid module 102 includes a finite element analysis module 103 for performing finite element analysis, as described in more detail below.

The system 100 also includes a voxel module 104 for dividing a volume into a plurality of voxels, the grid being contained by the volume. The surface of the volume, for example, can correspond to the surface of the grid. In a different example, the volume could be larger than the grid, such as a box enclosing the grid.

A sensitivity module 105 computes sensitivities, such that each voxel is assigned a sensitivity. In one embodiment, the sensitivity is approximately constant throughout the voxel. Typically, a voxel is larger than a finite element, containing several such elements (e.g., approximately one hundred). However, this need not be true in general.

The system 100 further includes a weight module 106 that uses a model of the body part to compute a set of weights associated with a particular one of the plurality of voxels. A diagnostic module 108 computes a diagnostic at the particular voxel to diagnose the possibility of disease in the body part, wherein the diagnostic is a function of the set of weights, and a measured electrical property of the body part obtained with the electrode array 12. An averaging module 110 calculates an average of a function $f(Z_i, Z_i^M)$, defined below, at the $k^{th}$ voxel.

Figure 8:
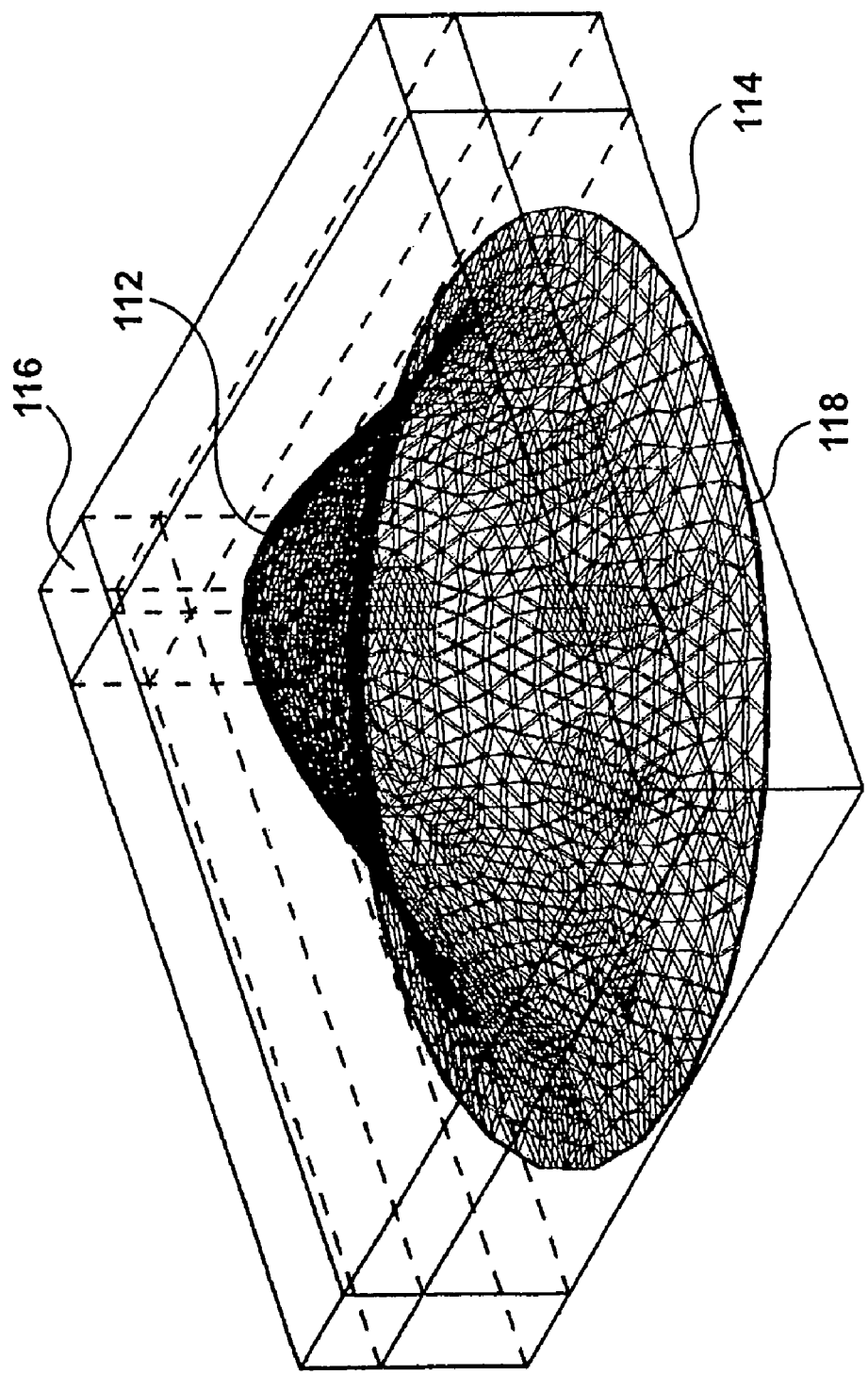
FIG. 8 is an illustration of three-dimensional grid and an enclosing volume formed by the grid module and voxel module, respectively, of FIG. 7.

FIG. 8 shows a three-dimensional grid 112 and an enclosing volume 114 formed by the grid module 102 and voxel module 104, respectively, of FIG. 7. The volume 114 is box shaped and is divided into smaller box-shaped voxels 116. The voxels 116 span the volume, but in FIG. 8 only a few voxels are shown for clarity. As described in more detail below, to each voxel is assigned a sensitivity. In one embodiment, the sensitivity is approximately constant throughout the voxel 116. The grid 112 is divided into a collection of finite elements 118, which in the example shown are three-dimensional triangular wedges. Again, for clarity, only a few finite elements 118 are shown. Typically, a voxel 116 is larger than a finite element 118.

The finite element analysis module 103 computes $\nabla V_{i,a}$, the gradient of the electric potential arising when conditions are employed corresponding to injection of current between the ith pair of current injection electrodes. The finite element analysis module 103 also computes $\nabla V_{i,b}$, the gradient of the electric potential arising when conditions are employed corresponding to injection of current between the pair of voltage electrodes associated with the ith pair of current injection electrodes.

The sensitivity module 105 uses the gradients $\nabla V_{i,a}$ and $\nabla V_{i,b}$ within a $k^{th}$ voxel to obtain a set of sensitivities, $\{\Delta u_{1k}, \Delta u_{2k}, \ldots, \Delta u_{n_{CI}k}\}$, where $\Delta u_{ik}$ is the sensitivity at the $k^{th}$ voxel obtained from $\nabla V_{i,a}$ and $\nabla V_{i,b}$. The set of weights are calculated by the weight module 106 according to $$w_{ik} = \frac{\Delta u_{ik}}{\sum_{j=1}^{n_{CI}} \Delta u_{jk}}.$$

The sensitivity module 105 obtains the sensitivity $\Delta u_{ik}$ using the formula $$\Delta u_{ik} = \int\int\int_{R_k} \Delta \kappa_{R_i} \nabla V_{ia} \cdot \nabla V_{ib} \, dv,$$

where $R_k$ is the volume of the kth voxel, and $\Delta \kappa_{R_k}$ is a deviation of a conductivity at the kth voxel.

Diagnosing the possibility of disease in a body part using the sensitivity proceeds in a similar manner as above, but with sensitivities being used instead of current densities.

Thus, the grid module 102 uses the model of the body part to obtain a set of baseline impedances $\{Z_1, Z_2, \ldots, Z_{n_{CI}}\}$ where $Z_i$ is the impedance associated with the $i^{th}$ electrode pair.

The averaging module 110 of FIG. 7 calculates an average of a function $f(Z_i, Z_i^M)$ at the $k^{th}$ voxel, the average given by $$\langle f_k \rangle = \sum_{i=1}^{n_{CI}} w_{ik} f(Z_i, Z_i^M).$$

The diagnostic at the $k^{th}$ voxel is defined to be $\langle f_k \rangle$. For example, $$f(Z_i, Z_i^M) = \frac{Z_i}{Z_i^M}.$$

where the $Z_i^M$ are the impedances measured with the electrode array, as described above.

The electrode array 12, the grid module 102, the sensitivity module 105 and the weight module 106 are used to calculate diagnostics at the other voxels, which together with the particular one, comprise the plurality of voxels. The diagnostic module averages the diagnostics at the voxels 116 to find an averaged diagnostic $\langle f \rangle$, and calculates a second averaged diagnostic, $\langle f_{homo} \rangle$, corresponding to a homologous body part.

The diagnostic module 108 can calculate several quantities having diagnostic value, such as the difference $\langle f \rangle - \langle f_{homo} \rangle$ or $$\frac{\langle f \rangle - \langle f_{homo} \rangle}{\frac{1}{2}(\langle f \rangle + \langle f_{homo} \rangle)}$$

that are indicative of the possibility of disease in the body part or the homologous body part.

Figure 9:
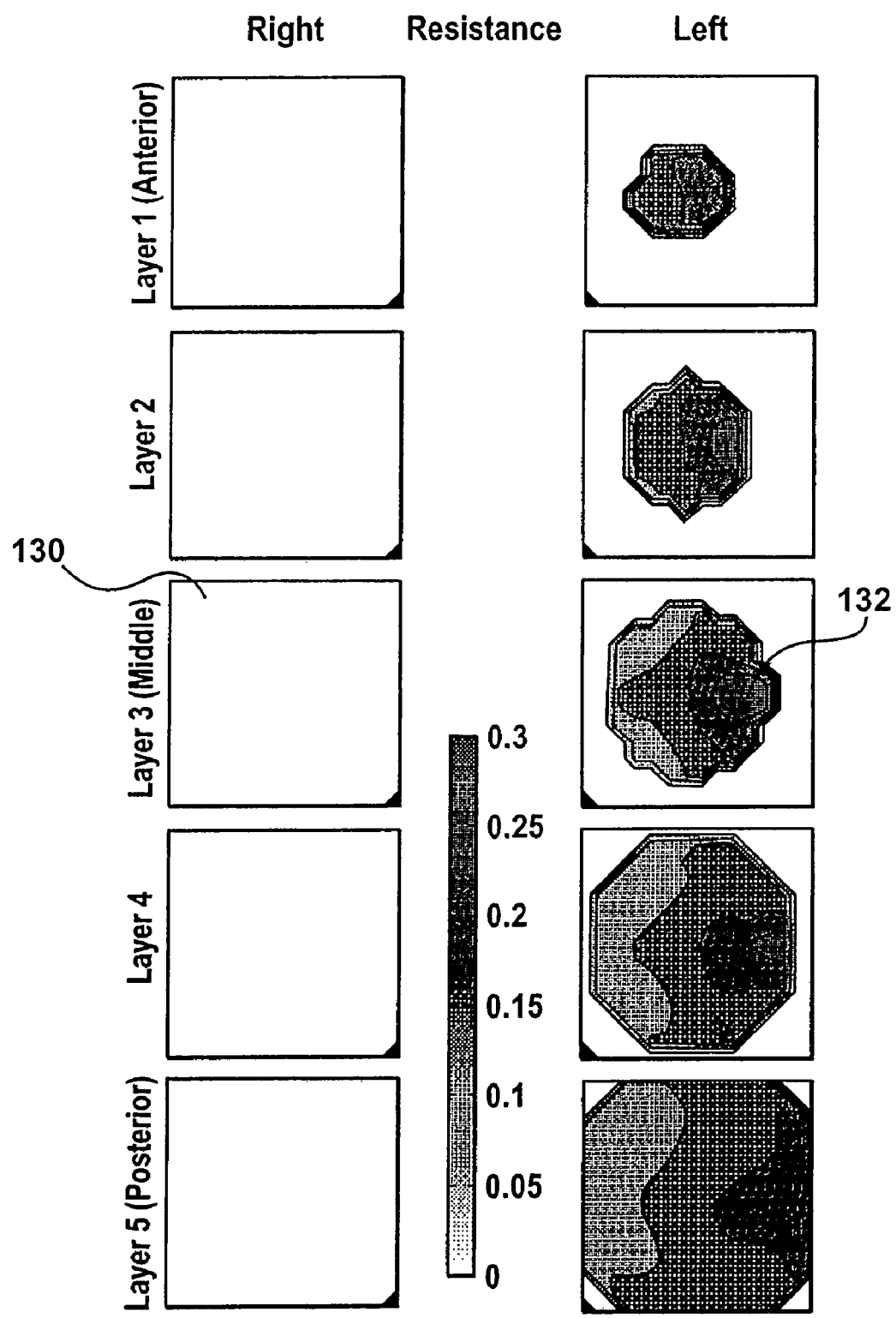
FIG. 9 is a plot showing images of different layers (i.e. slices) of respective right and left breasts of an actual subject that were obtained using a system in accordance with an embodiment of the invention.

Referring to FIG. 9, shown is a plot of images of different layers (i.e. slices) of respective right and left breasts of an actual subject that were obtained using a system in accordance with an embodiment of the invention. The subject has a carcinoma in the left breast, which is generally indicated by 132. The first layer (i.e. anterior, top layer) is the front-most layer. The gray patterns in the plot represent a relative difference between two homologous areas between right and left breasts. That is the darkness or intensity of a grey pattern increases as the homologous difference of the diagnostic becomes more profound. The carcinoma 132 is the darkest grey pattern in the left breast. More specifically, the carcinoma 132 is located at the middle depth at approximately three o'clock. The three o'clock angle is clearly visible in all layers while the darkest area deminates the plot of the middle layer. The right breast, on the other hand, is completely white because all of the corresponding WVG valves on the left breast are higher than those on the right breast.

The quantity $|\langle f_{right} \rangle - \langle f_{left} \rangle|$ is, by convention, plotted on the side having the larger WEVal; i.e., on the right breast for elements where $\langle f_{right} \rangle > \langle f_{left} \rangle$ and on the left breast where $\langle f_{left} \rangle > \langle f_{right} \rangle$. These differences are scaled in the figure to the maximum level of black. Sixteen different levels of gray are presented, and some contrasting has been added to emphasize areas where the differences are highest. However, none of these scaling methods appreciably influenced the results.

Different computer systems can be used to implement the method for diagnosing disease in a body part. The computer system can include a monitor for displaying diagnostic information using one of several visual methods. In one embodiment, the method can be implemented on a 2 GHz Pentium™ 4 system with 512 MB RAM.

Although emphasis has been placed on describing a system for diagnosing breast cancer, the principles of the present invention can also be advantageously applied to other diseases of other body parts. These body parts need not have a homolog. Also, although the main measured electrical property described herein is impedance, it should be understood that other electrical properties, such as functions of the electrical impedance, may also be used in accordance with the principles of the present invention.

The expression for the voltage across a lead b for a unit current injection over lead a is:

$$\begin{aligned}
u_{a,b} &= \frac{\iint_{\beta_2} V_a \, ds}{\iint_{\beta_2} 1 \cdot ds} - \frac{\iint_{\beta_1} V_a \, ds}{\iint_{\beta_1} 1 \cdot ds} \\
&= -\iint_{\beta_2} V_a J_b \cdot ds - \quad \frac{1}{\iint_{\beta_1} 1 \cdot ds} = i = \iint_{\beta_1} J_b \cdot ds \\
&\quad \iint_{\beta_1} V_a J_b \cdot ds \\
&= -\iint_S V_a J_b \cdot ds \quad J_b \cdot ds = 0 \text{ on } S \text{ which is not in} \\
&\quad (\beta_1 \cup \beta_2) \\
&= -\iiint_B \nabla \cdot (V_a J_b) dv \quad \text{Divergence Theorem: } \iint_S G \cdot ds = \\
&\quad \iiint_B \nabla \cdot G \, dv, B \text{ is volume} \\
&= -\iiint_B V_a \nabla \cdot J_b \, dv - \quad \text{product rule of differentiation} \\
&\quad \iiint_B J_b \cdot \nabla V_a \, dv \\
&= -\iiint_B J_b \cdot \nabla V_a \, dv \quad \nabla \cdot J_b = 0 \text{ on volume } B \\
&= \iiint_B k \nabla V_a \cdot \nabla V_b \, dv \quad J_b = -k \nabla V_b
\end{aligned}$$

It should be understood that various modifications and adaptations could be made to the embodiments described and illustrated herein, without departing from the present invention, the scope of which is defined in the appended claims.

What is claimed is:

1. A method for diagnosing a possibility of disease in a body part, the method comprising:
   representing the body part with a grid having a plurality of finite elements, the grid contained within a volume;
   dividing the volume into a plurality of voxels;
   obtaining a set of weights associated with a particular one of the voxels using a model of the body part, each weight in the set of weights obtained by computing a baseline quantity in the particular one of the voxels for a corresponding current injection in a plurality of current injections into the body part using an electrode array;
   computing a diagnostic at the particular one of the voxels, the diagnostic computed as an average of a function weighted over the plurality of current injections using the set of weights, and the function used to compute the diagnostic defined in relation to a measured electrical property of the body part obtained with the electrode array; and
   utilizing the diagnostic to diagnose the possibility of disease in the body part.

2. The method of claim 1, further comprising obtaining a baseline electrical property associated with the body part using the model of the body part, wherein the function used to compute the diagnostic is defined further in terms of the baseline electrical property.

3. The method of claim 1, wherein the measured electrical property is conditioned to compute the diagnostic.

4. The method of claim 1, wherein the measured electrical property is an impedance.

5. The method of claim 1, wherein the baseline electrical property is obtained using a physical model of the body part.

6. The method of claim 2, wherein the baseline electrical property is obtained using a control subject.

7. The method of claim 2, wherein the baseline electrical property is obtained using a finite element method.

8. The method of claim 7, wherein the baseline electrical property is obtained by
obtaining a baseline voltage; and
using the baseline voltage to compute a baseline impedance.

9. The method of claim 8, wherein, in the step of obtaining a baseline electrical property, the model of the body part assumes a non-uniform resistivity.

10. The method of claim 2, further comprising
applying a plurality of electrodes to the body part; and
obtaining the measured electrical property of the body part with the plurality of electrodes.

11. The method of claim 10, wherein the step of applying a plurality of electrodes comprises:
applying $n_e$ current injection electrodes on the body part, where $n_e$ is an integer greater than zero; and
applying $n_e$ voltage measurement electrodes on the body part, each of the current injection electrodes associated with one of the voltage measurement electrodes.

12. The method of claim 11, wherein the step of obtaining the measured electrical property comprises:
injecting a current between a current injection electrode pair;
measuring a resultant voltage difference between a voltage measurement electrode pair associated with the current injection electrode pair;
repeating the steps of injecting a current and measuring a resultant voltage difference for other current injection electrode pairs and associated voltage measurement electrode pairs until $n_{Cl}$ voltage differences $\{V_1^M, V_2^M, \ldots, V_{ndi\ Cl}^M\}$ are obtained; and
using the $n_{Cl}$ voltage differences to obtain associated measured impedances $\{Z_1^M, Z_2^M, \ldots, Z_{n_{Cl}}^M\}$, where $Z_j^M$ is a measured impedance obtained by using a $j^{th}$ current injection electrode pair and an associated $j^{th}$ voltage measurement electrode pair.

13. The method of claim 12, wherein, if the particular one of the voxels is identified as a $k^{th}$ voxel and the set of weights is denoted by $\{w_{1k}, w_{2k}, \ldots, w_{n_{Cl}k}\}$, where $w_{ik}$ is a weight associated with the $k^{th}$ voxel and an $i^{th}$ current injection electrode pair, then the step of obtaining a set of weights comprises:
computing a gradient $\nabla V_{i,a}$ of the of electric potential arising due to injection of current between the $i^{th}$ pair of current injection electrode pair;
computing a gradient $\nabla V_{i,b}$ of the of electric potential arising due to injection of current between an $i^{th}$ voltage measurement electrode pair associated with the $i^{th}$ current injection electrode pair;
obtaining a set of sensitivities $\{\Delta u_{1k}, \Delta u_{2k}, \ldots, \Delta u_{n_{Cl}k}\}$, where $\Delta u_{ik}$ is a sensitivity at the $k^{th}$ voxel obtained from the gradients $\nabla V_{i,a}$ and $\nabla V_{i,b}$; and
obtaining the set of weights using the relation $$w_{ik} = \frac{\Delta u_{ik}}{\sum_{j=1}^{n_{Cl}} \Delta u_{jk}}.$$

14. The method of claim 13, wherein, in the step of obtaining a set of sensitivities, $\Delta u_{ik}$ is given by $$\Delta u_{ik} = -\int\int\int_{R_k} \Delta \kappa_{R_i} \nabla V_{ia} \cdot \nabla V_{ib} \, dv,$$

where $R_k$ is a volume of the $k^{th}$ voxel, and $\Delta \kappa_{R_i}$ is a deviation of a conductivity at the $k^{th}$ voxel.

15. The method of claim 13, wherein the step of obtaining a baseline electrical property comprises:
using the model of the body part to obtain a set of baseline impedances $\{Z_1, Z_2, \ldots, Z_{n_{Cl}}\}$, where $Z_i$ is an impedance associated with the $i^{th}$ current injection electrode pair and associated $i^{th}$ voltage measurement electrode pair.

16. The method of claim 15, wherein the step of computing a diagnostic comprises:
calculating an average of a function $f(Z_i, Z_i^M)$ at the $k^{th}$ voxel, the average given by $$\langle f_k \rangle = \sum_{i=1}^{n_{Cl}} w_{ik} f(Z_i, Z_i^M),$$

wherein the diagnostic at the $k^{th}$ voxel is defined to be $\langle f_k \rangle$.

17. The method of claim 16, wherein the function $f(Z_i, Z_i^M)$ is given by $$f(Z_i, Z_i^M) = \frac{Z_i}{Z_i^M}.$$

18. The method of claim 16, further comprising
obtaining diagnostics at each of the plurality of voxels, wherein the step of utilizing the diagnostic comprises:
averaging the diagnostics obtained at each of the plurality of voxels to find an averaged diagnostic $\langle f \rangle$; and
calculating a second averaged diagnostic $\langle f_{homo} \rangle$ corresponding to a homologous body part.

19. The method of claim 18, wherein the step of utilizing the diagnostic further comprises calculating a difference $\langle f \rangle - \langle f_{homo} \rangle$, wherein an absolute difference $|\langle f \rangle - \langle f_{homo} \rangle|$ is indicative of the possibility of disease in the body part or the homologous body part.

20. The method of claim 18, wherein the step of utilizing the diagnostic further comprises calculating a relative difference $$\frac{\langle f \rangle - \langle f_{homo} \rangle}{\frac{1}{2}(\langle f \rangle + \langle f_{homo} \rangle)}$$

wherein the relative difference is indicative of the possibility of disease in the body part or the homologous body part.

21. A method for obtaining a representation of a part of a human body in the form of an electrical network, the method comprising:
representing the body part with a grid having a plurality of finite elements, the grid contained within a volume;
dividing the volume into a plurality of voxels;
obtaining a set of weights associated with a particular one of the voxels using a model of the body part, each weight in the set of weights obtained by computing a baseline quantity in the particular one of the voxels for a corresponding current injection in a plurality of current injections into the body part using an electrode array; and computing a diagnostic at the particular one of the voxels, the diagnostic computed as an average of a function weighted over the plurality of current injections using the set of weights, and the function used to compute the diagnostic defined in relation to a measured electrical property of the body part obtained with the electrode array.

22. A system for diagnosing a possibility of disease in a body part, the system comprising:
   a grid module for representing the body part with a grid having a plurality of finite elements;
   a voxel module for dividing a volume into a plurality of voxels, the grid being contained by the volume;
   a weight module for using a model of the body part to compute a set of weights associated with a particular one of the plurality of voxels, each weight in the set of weights obtained by computing a baseline quantity in the particular one of the voxels for a corresponding current injection in a plurality of current injections into the body part using an electrode array; and
   a diagnostic module for computing a diagnostic at the particular one of the voxels to diagnose the possibility of disease in the body part, wherein the diagnostic module is configured to compute the diagnostic as an average of a function weighted over the plurality of current injections using the set of weights, and the function used to compute the diagnostic is defined in relation to a measured electrical property of the body part obtained with the electrode array.

23. A system for obtaining a representation of a part of a human body in the form of an electrical network, the system comprising:
   a grid module for representing the body part with a grid having a plurality of finite elements;
   a voxel module for dividing a volume into a plurality of voxels, the grid being contained by the volume;
   a weight module for using a model of the body part to compute a set of weights associated with a particular one of the plurality of voxels, each weight in the set of weights obtained by computing a baseline quantity in the particular one of the voxels for a corresponding current injection in a plurality of current injections into the body part using an electrode array; and
   a diagnostic module for computing a diagnostic at the particular one of the voxels to diagnose the possibility of disease in the body part, wherein the diagnostic module is configured to compute the diagnostic as an average of a function weighted over the plurality of current injections using the set of weights, and the function used to compute the diagnostic is defined in relation to a measured electrical property of the body part obtained with the electrode array.

* * * * *